United States Patent
Hidaka et al.

(10) Patent No.: US 11,374,259 B2
(45) Date of Patent: *Jun. 28, 2022

(54) ELECTROLYTIC SOLUTION, ELECTROCHEMICAL DEVICE, SECONDARY CELL, AND MODULE

(71) Applicant: DAIKIN INDUSTRIES, LTD., Osaka (JP)

(72) Inventors: Tomoya Hidaka, Osaka (JP); Kenzou Takahashi, Osaka (JP); Masakazu Kinoshita, Osaka (JP); Shigeaki Yamazaki, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 158 days.

This patent is subject to a terminal disclaimer.

(21) Appl. No.: 16/626,754

(22) PCT Filed: May 30, 2018

(86) PCT No.: PCT/JP2018/020786
§ 371 (c)(1),
(2) Date: Dec. 26, 2019

(87) PCT Pub. No.: WO2019/003776
PCT Pub. Date: Jan. 3, 2019

(65) Prior Publication Data
US 2020/0127331 A1    Apr. 23, 2020

(30) Foreign Application Priority Data

Jun. 30, 2017   (JP) .............................. JP2017-128995

(51) Int. Cl.
| | | |
|---|---|---|
| *H01M 10/0567* | (2010.01) | |
| *C07D 307/33* | (2006.01) | |
| *H01G 11/60* | (2013.01) | |
| *H01G 11/62* | (2013.01) | |
| *H01M 10/0569* | (2010.01) | |

(52) U.S. Cl.
CPC ...... *H01M 10/0567* (2013.01); *C07D 307/33* (2013.01); *H01G 11/60* (2013.01); *H01G 11/62* (2013.01); *H01M 10/0569* (2013.01); *H01M 2300/0025* (2013.01)

(58) Field of Classification Search
None
See application file for complete search history.

(56) References Cited

U.S. PATENT DOCUMENTS

| | | |
|---|---|---|
| 2008/0118843 A1 | 5/2008 | Tarnopolsky |
| 2011/0136018 A1 | 6/2011 | Nogi et al. |
| 2014/0023916 A1 | 1/2014 | Koh et al. |
| 2015/0200423 A1 | 7/2015 | Mita et al. |
| 2016/0351957 A1 | 12/2016 | Taeda et al. |
| 2019/0214682 A1 | 7/2019 | Sakata et al. |
| 2020/0127331 A1 | 4/2020 | Hidaka et al. |
| 2020/0127332 A1 | 4/2020 | Hidaka et al. |

FOREIGN PATENT DOCUMENTS

| | | |
|---|---|---|
| EP | 2 320 510 A1 | 5/2011 |
| EP | 2 498 329 A1 | 9/2012 |
| EP | 2 503 633 A2 | 9/2012 |
| EP | 2 887 439 A1 | 6/2015 |
| EP | 3 483 974 A1 | 5/2019 |
| JP | 2001-57237 A | 2/2001 |
| JP | 2008-130544 A | 6/2008 |
| JP | 5274563 B2 | 8/2013 |
| JP | 2014-522078 A | 8/2014 |
| JP | 2015-133278 A | 7/2015 |
| KR | 10-2016-0049077 A | 5/2016 |
| WO | 2012/133902 A1 | 10/2012 |
| WO | 2012/170688 A2 | 12/2012 |
| WO | 2015/146685 A1 | 10/2015 |
| WO | 2018/016245 A1 | 1/2018 |
| WO | 2018/016246 A1 | 1/2018 |

OTHER PUBLICATIONS

Extended European Search Report dated Jan. 12, 2021 from the European Patent Office in counterpart EP Application No. 18823462.9.
Partial Supplementary European Search Report dated Jan. 13, 2021 from the European Patent Office in related EP Application No. 18823919.8.
International Search Report for PCT/JP2018/020786 dated Jul. 31, 2018 [PCT/ISA/210].
International Search Report for PCT/JP2018/020793 dated Jul. 31, 2018 [PCT/ISA/210].
Extended European Search Report dated Apr. 1, 2021, issued by the European Patent Office in related application No. 18823919.8.
International Preliminary Report on Patentability with a Translation of Written Opinion in International Application No. PCT/JP2018/020786, dated Dec. 31, 2019.
International Preliminary Report on Patentability with a Translation of Written Opinion in International Application No. PCT/JP2018/020793, dated Dec. 31, 2019.
Office Action dated Mar. 18, 2022, issued by the U.S. Patent and Trademark Office in U.S. Appl. No. 16/626,755.

*Primary Examiner* — Laura Weiner

(74) *Attorney, Agent, or Firm* — Sughrue Mion, PLLC

(57) ABSTRACT

An electrolyte solution contains tris(trimethylsilyl) phosphite and at least one fluorinated saturated cyclic carbonate (1) selected from pentafluoropropylethylene carbonate and heptafluoroisobutylethylene carbonate. Also disclosed is an electrochemical device including the electrolyte solution.

8 Claims, No Drawings

ELECTROLYTIC SOLUTION, ELECTROCHEMICAL DEVICE, SECONDARY CELL, AND MODULE

CROSS REFERENCE TO RELATED APPLICATIONS

This application is a National Stage of International Application No. PCT/JP2018/020786 filed May 30, 2018, claiming priority based on Japanese Patent Application No. 2017-128995 filed Jun. 30, 2017.

TECHNICAL FIELD

The invention relates to electrolyte solutions, electrochemical devices, secondary batteries, and modules.

BACKGROUND ART

Current electric appliances demonstrate a tendency to have a reduced weight and a smaller size, which leads to development of lithium-ion secondary batteries having a high energy density. Further, lithium-ion secondary batteries are desired to have improved battery characteristics as they are applied to more various fields. Battery characteristics will become more and more important particularly when lithium-ion secondary batteries are put in use for automobiles.

Patent Literature 1 discloses a secondary battery including a positive electrode, a negative electrode, and a non-aqueous electrolyte solution, wherein the positive electrode includes an electrode compound which absorbs and releases an electrode reactant at a potential of 4.5 V or higher (potential versus lithium), and the non-aqueous electrolyte solution includes a silyl compound where one or two or more silicon-oxygen-containing groups ($SiR_3$—O—: the three Rs are each any one of a monovalent hydrocarbon group and a halogenated group thereof) are bonded with an atom other than silicon.

Patent Literature 2 discloses an electrolyte solution for a high voltage battery, containing a lithium salt, a non-aqueous solvent, and a compound represented by the formula (I):

[Chem. 1]

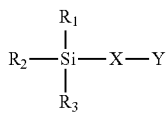

(I)

(wherein $R_1$, $R_2$, and $R_3$ are independently selected from the group consisting of substituted and unsubstituted $C_1$-$C_{20}$ alkyl groups, substituted and unsubstituted $C_1$-$C_{20}$ alkenyl groups, substituted and unsubstituted $C_1$-$C_{20}$ alkynyl groups, and substituted and unsubstituted $C_5$-$C_{20}$ aryl groups; X is nitrogen or oxygen; and Y is selected from the group consisting of hydride groups, halo groups, hydroxy groups, thio groups, alkyl groups, alkenyl groups, alkynyl groups, aryl groups, iminyl groups, alkoxy groups, alkenoxy groups, alkynoxy groups, aryloxy groups, carboxy groups, alkylcarbonyloxy groups, alkenylcarbonyloxy groups, alkynylcarbonyloxy groups, arylcarbonyloxy groups, alkylthio groups, alkenylthio groups, alkynylthio groups, arylthio groups, cyano groups, N-substituted amino groups, alkylcarbonylamino groups, N-substituted alkylcarbonylamino groups, alkenylcarbonylamino groups, N-substituted alkenyl carbonylamino groups, alkynylcarbonyl amino groups, N-substituted alkynylcarbonylamino groups, arylcarbonylamino groups, N-substituted arylcarbonylamino groups, boron-containing groups, aluminum-containing groups, silicon-containing groups, phosphorus-containing groups, and sulfur-containing groups), wherein the electrolyte solution is characterized by electrochemical stability in a high voltage battery at voltages above about 4.2 V.

Patent Literature 3 discloses a non-aqueous electrolyte solution for a lithium secondary battery, including 0.01 to 15% by mass of an organosilicon compound represented by the following formula [1] and 0.1 to 3 mol/L of a fluorine-containing alkali metal salt that is an electrolyte, wherein the amount of a fluorinated organosilicon compound generated by reaction of the organosilicon compound and the fluorine-containing alkali metal salt is 0.2% by mass or less,

[Chem. 2]

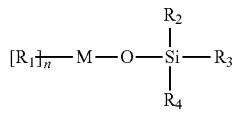

[1]

wherein M is a metal atom, a phosphorus atom, a boron atom, or P=O; $R_1$ is a C1-C11 alkyloxy group, a silyloxy group, or a C1-C11 alkylsilyloxy group; n is the number of $R_1$ that is bonded to M, and is equal to the oxidation number of M minus 1 or the oxidation number of M minus 3; when n is 2 or greater, the two or more of $R_1$ may be the same as or different from each other; and $R_2$ to $R_4$ are each independently a C1-C11 alkyl group, a C1-C11 alkenyl group, a C1-C11 alkyloxy group, or a C6-C11 aryl group.

Patent Literature 4 discloses an electrolyte for a lithium secondary battery, including:
a compound represented by the following formula 1:

$A-[OSi(C_mH_{2m+1})_3]_3$       [formula 1]

(wherein A is phosphorus (P) or boron (B); and m is an integer of 0 to 6);
a lithium salt; and
a non-aqueous organic solvent.

Patent Literature 5 discloses a non-aqueous electrolyte solution for a lithium secondary battery containing an electrolyte and a non-aqueous solvent that contains a compound represented by the following formula [1]:

[Chem. 3]

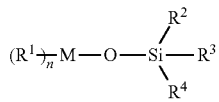

[1]

wherein M is a metal element, phosphorus, or boron; $R^1$ is a C1-C11 alkyloxy group or a silyloxy group; when n is 2 or greater, the two or more of $R^1$ may be the same as or different from each other; $R^2$, $R^3$, and $R^4$ are the same as or different from each other, and are each a C1-C11 alkyl, alkenyl, aryl, or alkyloxy group; and n is the number of $R^1$ that is bonded to M, and is equal to the oxidation number of M minus 1.

CITATION LIST

Patent Literature

Patent Literature 1: JP 2015-133278 A
Patent Literature 2: JP 2014-522078 T
Patent Literature 3: JP 5274563 B
Patent Literature 4: JP 2008-130544 A
Patent Literature 5: JP 2001-57237 A

SUMMARY OF INVENTION

Technical Problem

Conventional electrolyte solutions cause an increase in resistance when they are used in electrochemical devices such as lithium ion secondary batteries and the electrochemical devices are stored at high temperature.

The invention is made in view of the above current state of the art, and aims to provide an electrolyte solution that can hardly increase the resistance of an electrochemical device such as a lithium ion secondary battery even after the electrochemical device is stored at high temperature in comparison with that before the storage.

The invention also aims to provide an electrochemical device such as a lithium ion secondary battery that can hardly have an increased resistance even after stored at high temperature in comparison with that before the storage.

Solution to Problem

The inventors performed studies to find that selecting tris(trimethylsilyl) phosphite as an organosilicon compound and selecting a specific fluorinated cyclic carbonate among many solvents and additives to combine them can solve the above issues, thereby completing the invention.

In other words, the invention relates to an electrolyte solution containing tris(trimethylsilyl) phosphite and at least one fluorinated saturated cyclic carbonate (1) selected from the group consisting of a compound (1-a) and a compound (1-b),
the compound (1-a) being represented by the following formula:

[Chem. 4]

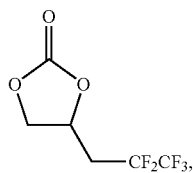

the compound (1-b) being represented by the following formula:

[Chem. 5]

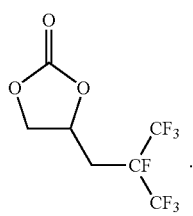

The electrolyte solution preferably further contains a solvent.

The solvent preferably contains at least one selected from the group consisting of a non-fluorinated saturated cyclic carbonate, a fluorinated saturated cyclic carbonate other than the fluorinated saturated cyclic carbonate (1), a non-fluorinated acyclic carbonate, a fluorinated acyclic carbonate, a non-fluorinated acyclic ester, and a fluorinated acyclic ester.

In the electrolyte solution, the tris(trimethylsilyl) phosphite is preferably present in an amount of 0.001 to 10% by mass relative to the solvent.

In the electrolyte solution, the fluorinated saturated cyclic carbonate (1) is preferably present in an amount of 0.001 to 10% by mass relative to the solvent.

The electrolyte solution preferably further contains vinylone carbonate.

Preferably, the electrolyte solution further contains a solvent and the vinylene carbonate is present in an amount of 0.001 to 10% by mass relative to the solvent.

The electrolyte solution preferably further contains an electrolyte salt.

The invention also relates to an electrochemical device including the above electrolyte solution.

The invention also relates to a secondary battery including the above electrolyte solution.

The invention also relates to a module including the above electrochemical device or the above secondary battery.

Advantageous Effects of Invention

The electrolyte solution of the invention can reduce an increase in resistance even after the electrochemical device is stored at high temperature.

The electrochemical device including the electrolyte solution of the invention can hardly have an increased resistance even after stored at high temperature.

DESCRIPTION OF EMBODIMENTS

The invention will be specifically described hereinbelow.

The electrolyte solution of the invention contains tris(trimethylsilyl) phosphite and at least one fluorinated saturated cyclic carbonate (1) selected from the group consisting of a compound (1-a) and a compound (1-b).

The tris(trimethylsilyl) phosphite is represented by the following formula.

[Chem. 6]

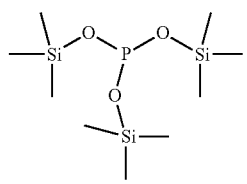

The compound (1-a) is represented by the following formula.

[Chem. 7]

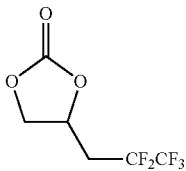

The formula (1-b) is represented by the following formula.

[Chem. 8]

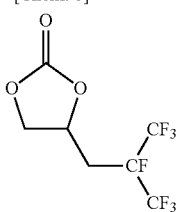

The electrolyte solution of the invention preferably contains a solvent.

When the electrolyte solution of the invention contains a solvent, the tris(trimethylsilyl) phosphite is preferably present in an amount of 0.001 to 10% by mass relative to the solvent. The amount is more preferably 0.01% by mass or more, still more preferably 0.1% by mass or more, while more are preferably 5% by mass or leas, still more preferably 1% by mass or less.

When the electrolyte solution of the invention contains a solvent, the fluorinated saturated cyclic carbonate (1) is preferably present in an amount of 0.001 to 10% by mass relative to the solvent. The amount is more preferably 0.01% by mass or more, still more preferably 0.1% by mass or more, while more preferably 5% by mass or less, still more preferably 1% by mass or less.

The solvent in the electrolyte solution is preferably present in an amount of 90% by volume or more, more preferably 95% by volume or more, while may be 99.9% by volume or less, relative to the electrolyte solution.

The solvent preferably contains at least one selected from the group consisting of a non-fluorinated saturated cyclic carbonate, a fluorinated saturated cyclic carbonate other than the fluorinated saturated cyclic carbonate (1), a non-fluorinated acyclic carbonate, a fluorinated acyclic carbonate, a non-fluorinated acyclic ester, and a fluorinated acyclic ester.

The solvent also preferably contains at least one cyclic carbonate selected from the group consisting of the non-fluorinated saturated cyclic carbonate and the fluorinated saturated cyclic carbonate other than the fluorinated saturated cyclic carbonate (1) and at least one acyclic compound selected from the group consisting of the non-fluorinated acyclic carbonate, the fluorinated acyclic carbonate, the non-fluorinated acyclic ester, and the fluorinated acyclic ester.

The cyclic carbonate and the acyclic compound in the solvent preferably have a volume ratio of 10/90 to 90/10, more preferably 20/80 or higher, still more preferably 25/75 or higher, while more preferably 70/30 or lower, still more preferably 50/50 or lower.

The solvent also preferably contains the non-fluorinated saturated cyclic carbonate and at least one non-fluorinated acyclic compound selected from the group consisting of the non-fluorinated acyclic carbonate and the non-fluorinated acyclic ester. This combination is suitable when the electrolyte solution is used for an electrochemical device that is driven at relatively low voltage.

The non-fluorinated saturated cyclic carbonate and the non-fluorinated acyclic compound in the solvent preferably have a volume ratio of 10/90 to 90/10, more preferably 20/80 or higher, still more preferably 25/75 or higher, while more preferably 70/30 or lower, still more preferably 50/50 or lower.

The solvent also preferably contains the fluorinated saturated cyclic carbonate other than the fluorinated saturated cyclic carbonate (1) and at least one fluorinated acyclic compound selected from the group consisting of the fluorinated acyclic carbonate and the fluorinated acyclic ester. This combination is suitable when the electrolyte solution is used for an electrochemical device that is driven at relatively high voltage.

The fluorinated saturated cyclic carbonate other than the fluorinated saturated cyclic carbonate (1) and the fluorinated acyclic compound in the solvent preferably have a volume ratio of 10/90 to 90/10, more preferably 20/80 or higher, still more preferably 25/75 or higher, while more preferably 70/30 or lower, still more preferably 50/50 or lower.

Examples of the non-fluorinated saturated cyclic carbonate include ethylene carbonate (EC), propylene carbonate (PC), and butylene carbonate.

In order to give a high permittivity and good viscosity, the non-fluorinated saturated cyclic carbonate preferably includes at least one compound selected from the group consisting of ethylene carbonate, propylene carbonate, and butylene carbonate.

For the non-fluorinated saturated cyclic carbonate, one of the above compounds may be used or two or more thereof may be used in combination.

The fluorinated saturated cyclic carbonate other than the fluorinated saturated cyclic carbonate (1) is a saturated cyclic carbonate with a fluorine atom added thereto. Specific examples thereof include a compound other than the fluorinated saturated cyclic carbonate (1) represented by the following formula (A):

[Chem. 9]

(A)

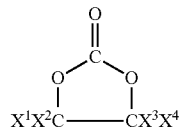

wherein $X^1$ to $X^4$ are the same as or different from each other, and are each —H, —$CH_3$, —$C_2H_5$, —F, a fluorinated alkyl group optionally containing an ether bond, or a fluorinated alkoxy group optionally containing an ether bond; at least one selected from $X^1$ to $X^4$ is —F, a fluorinated alkyl group optionally containing an ether bond, or a fluorinated alkoxy group optionally containing an ether bond.

The presence of the fluorinated saturated cyclic carbonate in the electrolyte solution of the invention when applied to a lithium-ion secondary battery, for example, enables formation of a stable film on the negative electrode and can thereby sufficiently reduce a side reaction of the electrolyte solution on the negative electrode. This results in significantly stable and excellent charge and discharge characteristics.

The term "ether bond" herein means a bond represented by —O—.

In order to give a good permittivity and oxidation resistance, one or two of $X^1$ to $X^4$ is/are each preferably —F, a fluorinated alkyl group optionally containing an ether bond, or a fluorinated alkoxy group optionally containing an ether bond.

In anticipation of a decrease in viscosity at low temperature, an increase in flash point, and improvement in solubility of an electrolyte salt, $X^1$ to $X^4$ are each preferably —H, —F, a fluorinated alkyl group (a), a fluorinated alkyl group (b) containing an ether bond, or a fluorinated alkoxy group (c).

The fluorinated alkyl group (a) is an alkyl group in which at least one hydrogen atom thereof is replaced by a fluorine atom. The fluorinated alkyl group (a) preferably has a carbon number of 1 to 20, more preferably 1 to 17, still more preferably 1 to 7, particularly preferably 1 to 5.

Too large a carbon number may cause poor low-temperature characteristics and low solubility of an electrolyte salt. Too small, a carbon number may cause low solubility of an electrolyte salt, low discharge efficiency, and increased viscosity, for example.

Examples of the fluorinated alkyl group (a) having a carbon number of 1 include $CFH_2-$, $CF_2H-$, and $CF_3-$. In order to give good high-temperature storage characteristics, $CF_2H-$ or $CF_3-$ is particularly preferred.

In order to give good solubility of an electrolyte salt, preferred examples of the fluorinated alkyl group (a) having a carbon number of 2 or greater include fluorinated alkyl groups represented by the following formula (a-1):

$$R^1-R^2- \quad (a-1)$$

wherein $R^1$ is an alkyl group having a carbon number of 1 or greater and optionally containing a fluorine atom; $R^2$ is a C1-C3 alkylene group optionally containing a fluorine atom; and at least one selected from $R^1$ and $R^2$ contains a fluorine atom.

$R^1$ and $R^2$ each may further contain an atom other than carbon, hydrogen, and fluorine atoms.

$R^1$ is an alkyl group having a carbon number of 1 or greater and optionally containing a fluorine atom, is preferably a C1-C16 linear or branched alkyl group. The carbon number of $R^1$ is more preferably 1 to 6, still more preferably 1 to 3.

Specifically, for example, $CH_3-$, $CH_3CH_2-$, $CH_3CH_2CH_2-$, $CH_3CH_2CH_2CH_2-$, and groups represented by the following formulae:

[Chem. 10]

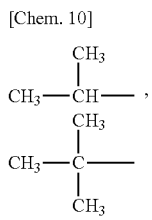

may be mentioned as linear or branched alkyl groups for $R^1$.

Examples of $R^1$ which is a linear alkyl group containing a fluorine atom include $CF_3-$, $CF_3CH_2-$, $CF_3CF_2-$, $CF_3CH_2CH_2-$, $CF_3CF_2CH_2-$, $CF_3CF_2CF_2-$, $CF_3CH_2CF_2-$, $CF_3CH_2CH_2CH_2-$, $CF_3CF_2CH_2CH_2-$, $CF_3CF_2CF_2CH_2-$, $CF_3CF_2CF_2CF_2-$, $CF_3CF_2CH_2CF_2-$, $CF_3CH_2CH_2CH_2CH_2-$, $CF_3CF_2CH_2CH_2CH_2-$, $CF_3CH_2CF_2CH_2CH_2-$, $CF_3CF_2CF_2CH_2$ $CH_2CH_2-$, $CF_3CF_2CF_2CF_2CH_2-$, $CF_3CF_2CH_2CF_2CH_2-$, $CF_3CF_2CH_2CH_2CH_2CH_2-$, $CF_3CF_2CF_2CF_2CH_2CH_2-$, $CF_3CF_2CH_2CF_2CH_2CH_2-$, $HCF_2-$, $HCF_2CH_2-$, $HCF_2$ $CF_2-$, $HCF_2CH_2CH_2-$, $HCF_2CF_2CH_2-$, $HCF_2CH_2$ $CF_2-$, $HCF_2CF_2CH_2CH_2-$, $HCF_2CH_2CF_2CH_2-$, $HCF_2$ $CF_2CF_2-$, $HCF_2CF_2CH_2CH_2-$, $HCF_2CH_2CF_2CH_2$ $CH_2-$, $HCF_2CF_2CF_2CF_2CH_2-$, $HCF_2CF_2CF_2CF_2CH_2$ $CH_2-$, $FCH_2-$, $FCH_2CH_2-$, $FCH_2CF_2-$, $FCH_2CF_2$ $CH_2-$, $FCH_2CF_2CF_2-$, $CH_3CF_2CH_2-$, $CH_3CF_2CF_2-$, $CH_3CF_2CH_2CF_2-$, $CH_3CF_2CF_2CF_2-$, $CH_3CH_2CF_2$ $CF_2-$, $CH_3CF_2CH_2CF_2CH_2-$, $CH_3CF_2CF_2CF_2CH_2-$, $CH_3CF_2CF_2CH_2CH_2-$, $CH_3CH_2CF_2CF_2CH_2-$, $CH_3CF_2$ $CH_2CF_2CH_2CH_2-$, $CH_3CF_2CH_2CF_2CH_2CH_2-$, HCF-$ClCF_2CH_2-$, $HCF_2CFClCH_2-$, $HCF_2CFClCF_2CFCl-$ $CH_2-$, and $HCFClCF_2CFClCF_2CH_2-$.

Examples of $R^1$ which is a branched alkyl group containing a fluorine atom include those represented by the following formulae.

[Chem. 11]

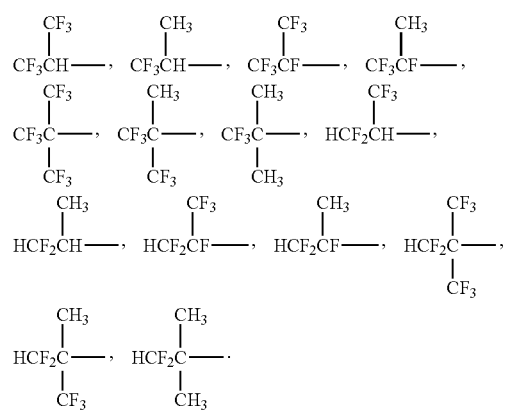

[Chem. 12]

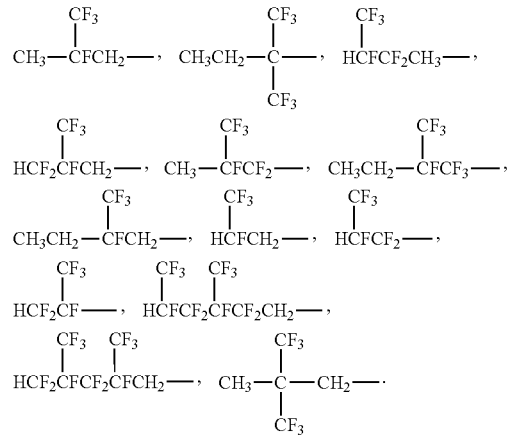

The presence of a branch such as $CH_3-$ or $CF_3-$ may easily cause high viscosity. Thus, the number of such branches is more preferably small (one) or zero.

$R^2$ is a C1-C3 alkylene group optionally containing a fluorine atom. $R^2$ may be either linear or branched.

Examples of a minimum structural unit, constituting such a linear or branched alkylene group are shown below. $R^2$ is constituted by one or combination of these units.
(i) Linear Minimum Structural Units

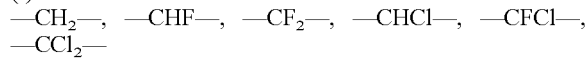

—CCl$_2$—
(ii) Branched Minimum Structural Units

[Chem. 13]

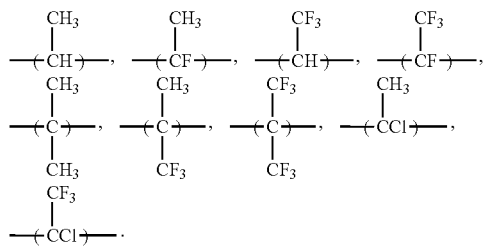

Preferred among these exemplified units are Cl-free structural units because such units may not be dehydrochlorinated by a base, and thus may be more stable.

$R^2$ which is a linear group consists only of any of the above linear minimum structural units, and is preferably —CH$_2$—, —CH$_2$CH$_2$—, or CF$_2$—. In order to further improve the solubility of an electrolyte salt, —CH$_2$— or —CH$_2$CH$_2$— is more preferred.

$R^2$ which is a branched group includes at least one of the above branched minimum structural units. A preferred example thereof is a group represented by —(CX$^a$X$^b$)— (wherein X$^a$ is H, F, CH$_3$, or CF$_3$; X$^b$ is C$_3$ or CF$_3$; when X$^b$ is CH$_3$, X$^a$ is H or CH$_3$). Such a group can much further improve the solubility of an electrolyte salt.

For example, CF$_3$CF$_2$—, HCF$_2$CF$_2$—, H$_2$CFCF$_2$—, CH$_3$CF$_2$—, CF$_3$CHF—, CH$_3$CF$_2$—, CF$_3$CF$_2$CF$_2$—, HCF$_2$CF$_2$CF$_2$—, H$_2$CFCF$_2$CF$_2$—, CH$_3$CF$_2$CF$_2$—, and those represented by the following formulae:

[Chem. 14]

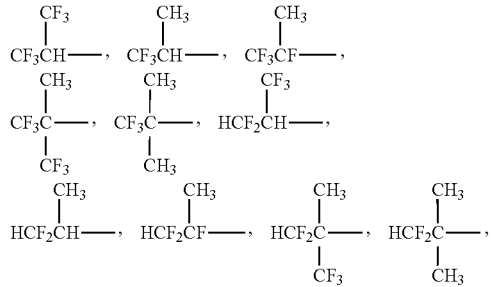

[Chem. 15]

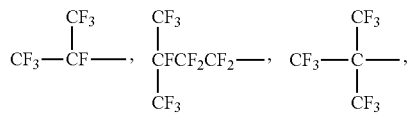

may be mentioned as preferred examples of the fluorinated alkyl group (a).

The fluorinated alkyl group (b) containing an ether bond is an alkyl group containing an ether bond in which at least one hydrogen atom thereof is replaced by a fluorine atom. The fluorinated alkyl group (b) containing an ether bond preferably has a carbon number of 2 to 17. Too large a carbon number may cause high viscosity of the fluorinated saturated cyclic carbonate. This may also cause the presence of many fluorine-containing groups, resulting in poor solubility of an electrolyte salt due to reduction in permittivity, and poor miscibility with other solvents. Accordingly, the carbon number of the fluorinated alkyl group (b) containing an ether bond is preferably 2 to 10, more preferably 2 to 7.

The alkylene group which constitutes the ether moiety of the fluorinated alkyl group (b) containing an ether bond is a linear or branched alkylene group. Examples of a minimum structural unit constituting such a linear or branched alkylene group are shown below.
(i) Linear Minimum Structural Units

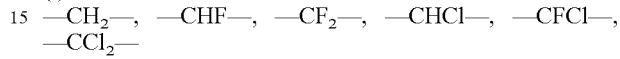

—CCl$_2$—
(ii) Branched Minimum Structural Units

[Chem. 16]

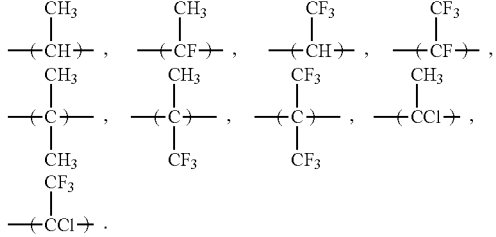

The alkylene group may be constituted by one of these minimum structural units, or may be constituted by multiple linear units (i), by multiple branched units (ii), or by a combination of a linear unit (i) and a branched unit (ii). Preferred examples will be mentioned in detail later.

Preferred among these exemplified units are Cl-free structural, units because such units may not be dehydrochlorinated by a base, and thus may be more stable.

A still more preferred example of the fluorinated alkyl group (b) containing an ether bond is a group represented by the following formula (b-1):

$$R^3—(OR^4)_{n1}—\qquad(b-1)$$

wherein $R^3$ is preferably a C1-C6 alkyl group optionally containing a fluorine atom; $R^4$ is preferably a C1-C4 alkylene group optionally containing a fluorine atom; n1 is an integer of 1 to 3; and at least one selected from $R^3$ and $R^4$ contains a fluorine atom.

Examples of $R^3$ and $R^4$ include the following groups, and any appropriate combination of these groups can provide the fluorinated alkyl group (b) containing an ether bond represented by the formula (b-1). Still, the groups are not limited thereto.

(1) $R^3$ is preferably an alkyl group represented by X$^c$$_3$C—(R$^5$)$_{n2}$— wherein three X$^c$s are the same as or different from each other, and are each H or F; $R^5$ is a C1-C5 alkylene group optionally containing a fluorine atom; and n2 is 0 or 1.

When n2 is 0, $R^3$ may be CH$_3$—, CF$_3$—, HCF$_2$—, or H$_2$CF—, for example.

When n2 is 1, specific examples of $R^3$ which is a linear group include CF$_3$CH$_2$—, CF$_3$CF$_2$—, CF$_3$CH$_2$CH$_2$—, CF$_3$CF$_2$CH$_2$—, CF$_3$CF$_2$CF$_2$—, CF$_3$CH$_2$CF$_2$—, CF$_3$CH$_2$CH$_2$CH$_2$—, CF$_3$CF$_2$CH$_2$CH$_2$—, CF$_3$CH$_2$CF$_2$CH$_2$—, CF$_3$CF$_2$CF$_2$CH$_2$—, CF$_3$CF$_2$CF$_2$CF$_2$—, CF$_3$CF$_2$CH$_2$CF$_2$—, CF$_3$CH$_2$CH$_2$CH$_2$CH$_2$—, CF$_3$CF$_2$CH$_2$ CH$_2$CH$_2$—, CF$_3$CH$_2$CF$_2$CH$_2$CH$_2$—, CF$_3$CF$_2$CF$_2$CH$_2$CH$_2$—, CF$_3$CF$_2$CF$_2$CF$_2$CH$_2$—, CF$_3$CF$_2$CH$_2$CF$_2$CH$_2$—, CF$_3$CF$_2$CH$_2$CH$_2$CH$_2$CH$_2$—, CF$_3$CF$_2$CF$_2$CH$_2$CH$_2$—, CF$_3$CF$_2$CH$_2$CF$_2$CH$_2$CH$_2$—, HCF$_2$CH$_2$—, HCF$_2$CF$_2$—, HCF$_2$CH$_2$CH$_2$—, HCF$_2$CF$_2$CH$_2$—, HCF$_2$CH$_2$CF$_2$—, HCF$_2$CF$_2$CH$_2$CH$_2$—, HCF$_2$CH$_2$CF$_2$CH$_2$—, HCF$_2$CF$_2$CF$_2$CF$_2$—, HCF$_2$CF$_2$CH$_2$CH$_2$CH$_2$—, HCF$_2$CH$_2$CF$_2$CH$_2$CH$_2$—, HCF$_2$CF$_2$CF$_2$CF$_2$CH$_2$—, HCF$_2$CF$_2$CF$_2$CF$_2$CH$_2$CH$_2$—, FCH$_2$CH$_2$—, FCH$_2$CF$_2$—, FCH$_2$CF$_2$CH$_2$—, CH$_3$CF$_2$—, CH$_3$CH$_2$—, CH$_3$CF$_2$CH$_2$—, CH$_3$CF$_2$CF$_2$—, CH$_3$CH$_2$CH$_2$—, CH$_3$CF$_2$CH$_2$CF$_2$—, CH$_3$CF$_2$CF$_2$CF$_2$—, CH$_3$CH$_2$CF$_2$CF$_2$—, CH$_3$CH$_2$CH$_2$CH$_2$—, CH$_3$CF$_2$CH$_2$CF$_2$CH$_2$—, CH$_3$CF$_2$CF$_2$CF$_2$CH$_2$—, CH$_3$CF$_2$CF$_2$CH$_2$—, CH$_3$CH$_2$CF$_2$CF$_2$CH$_2$—, CH$_3$CF$_2$CH$_2$CF$_2$CH$_2$—, CH$_3$CH$_2$CF$_2$CF$_2$CH$_2$CH$_3$—, and CH$_3$CF$_2$CH$_2$CF$_2$CH$_2$CH$_3$—.

When n2 is 1, those represented by the following formulae:

[Chem. 17]

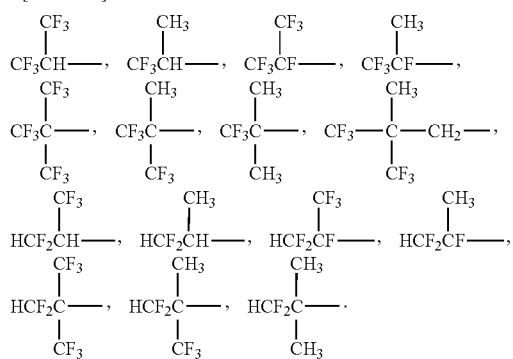

may be mentioned as examples of R$^3$ which is a branched group.

The presence of a branch such as CH$_3$— or CF$_3$— may easily cause high viscosity. Thus, R$^3$ is more preferably a linear group.

(2) In —(OR$^4$)$_{n1}$— of the formula (b-1), n1 is an integer of 1 to 3, preferably 1 or 2. When n1 is 2 or 3, R$^4$s may be the same as or different from each other.

Preferred specific examples of R$^4$ include the following linear or branched groups.

Examples of the linear groups include —CH$_2$—, —CHF—, —CF$_2$—, —CH$_2$CH$_2$—, —CF$_2$CH$_2$—, —CF$_2$CF$_2$—, —CH$_2$CF$_2$—, —CH$_2$CH$_2$CH$_2$—, —CH$_2$CH$_2$CF$_2$—, —CH$_2$CF$_2$CH$_2$—, —CH$_2$CF$_2$CF$_2$—, —CF$_2$CH$_2$CH$_2$—, —CF$_2$CF$_2$CH$_2$—, —CF$_2$CH$_2$CF$_2$, and —CF$_2$CF$_2$CF$_2$—.

Those represented by the following formulae:

[Chem. 18]

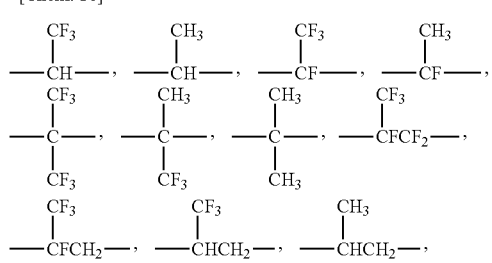

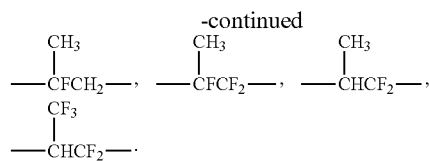

may be mentioned as examples of the branched groups.

The fluorinated alkoxy group (c) is an alkoxy group in which at least one hydrogen atom thereof is replaced by a fluorine atom. The fluorinated alkoxy group (c) preferably has a carbon number of 1 to 17. The carbon number is more preferably 1 to 6.

The fluorinated alkoxy group (c) is particularly preferably a fluorinated alkoxy group represented by X$^d_3$C—(R$^6$)$_{n3}$—O—, wherein three X$^d$s are the same as or different from each other, and are each H or F; R$^6$ is preferably a C1-C5 alkylene group optionally containing a fluorine atom; n3 is 0 or 1; and any of the three X$^d$s contain a fluorine atom.

Specific examples of the fluorinated alkoxy group (c) include fluorinated alkoxy groups in which an oxygen atom binds to an end of an alkyl group mentioned as an example for R$^1$ in the formula (a-1).

The fluorinated alkyl group (a), the fluorinated alkyl group (b) containing an ether bond, and the fluorinated alkoxy group (c) in the fluorinated saturated cyclic carbonate each preferably have a fluorine content, of 10% by mass or more. Too less a fluorine content may cause a failure in sufficiently achieving an effect of reducing the viscosity at low temperature and an effect of increasing the flash point. Thus, the fluorine content is more preferably 12% by mass or more, still more preferably 15% by mass or more. The upper limit thereof is usually 76% by mass.

The fluorine content of each of the fluorinated alkyl group (a), the fluorinated alkyl group (b) containing an ether bond, and the fluorinated alkoxy group (c) is a value calculated based on the corresponding structural formula by the following formula:

{(Number of fluorine atoms×19)/(Formula weight of group)}×100(%).

In order to give good permittivity and oxidation resistance, the fluorine content, in the whole fluorinated saturated cyclic carbonate is preferably 10% by mass or more, more preferably 15% by mass or more. The upper limit thereof is usually 76% by mass.

The fluorine content in the fluorinated saturated cyclic carbonate is a value calculated based on the structural formula of the fluorinated saturated cyclic carbonate by the following formula:

{(Number of fluorine atoms×19)/(Molecular weight of fluorinated saturated cyclic carbonate}×100 (%).

Specific examples of the fluorinated saturated cyclic carbonate include the following.

Specific examples of the fluorinated saturated cyclic carbonate in which at least one selected, from X$^1$ to X$^4$ is —F include those, represented by the following formulae.

[Chem. 19]

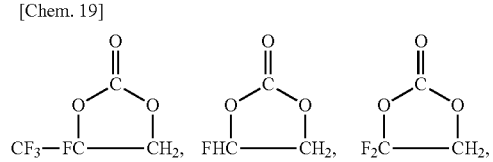

-continued

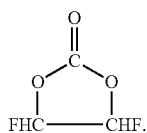

These compounds have a high withstand voltage and give good solubility of an electrolyte salt.

Alternatively, those represented by the following formulae:

[Chem. 20]

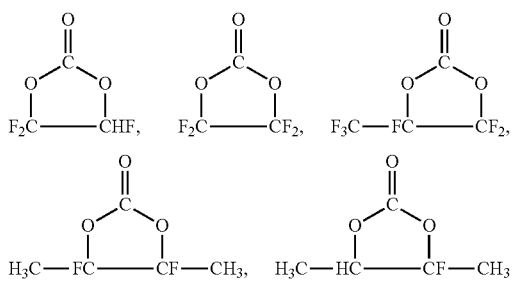

may also be used.

Those represented by the following formulae:

[Chem. 21]

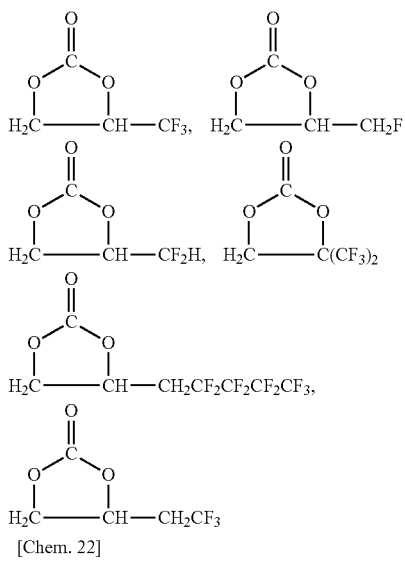

[Chem. 22]

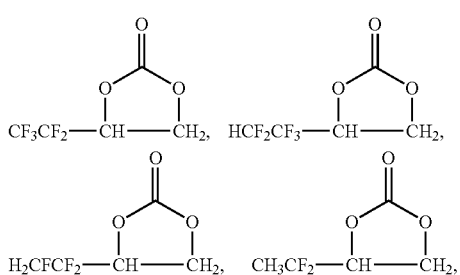

-continued

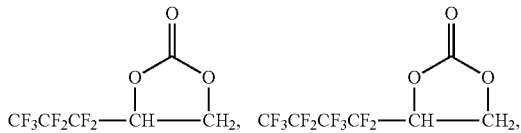

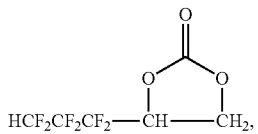

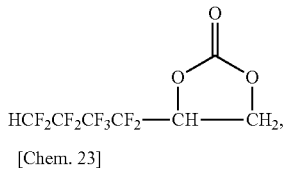

[Chem. 23]

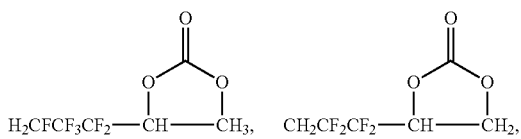

may be mentioned as specific examples of the fluorinated saturated cyclic carbonate in which at least one selected from $X^1$ to $X^4$ is a fluorinated alkyl group (a) and the others are —H.

Those represented by the following formulae:

[Chem. 24]

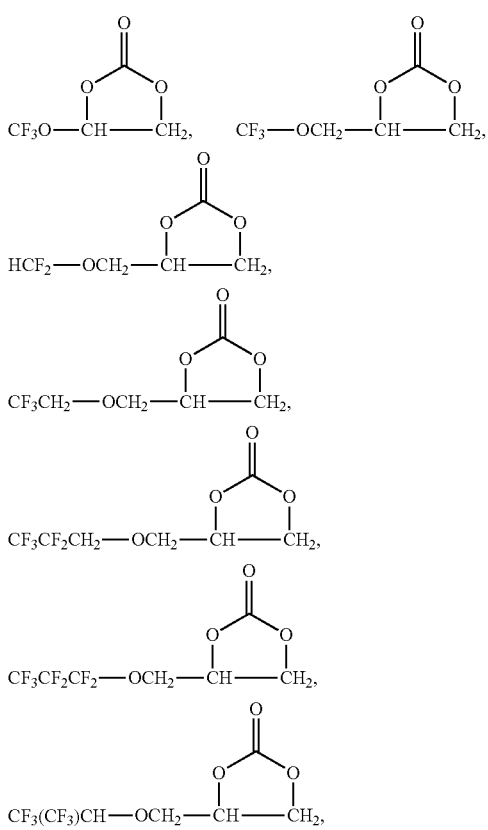

-continued
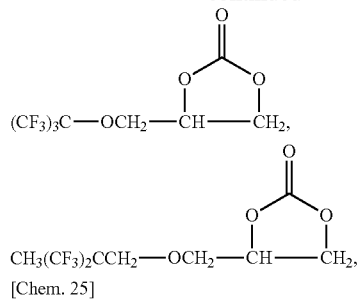
[Chem. 25]
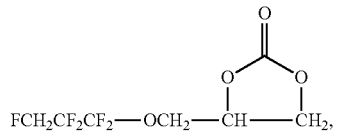
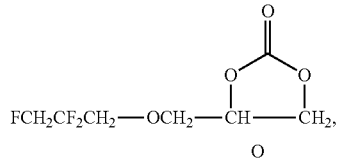
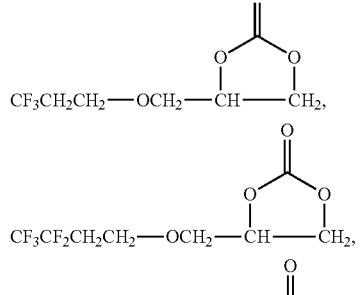
[Chem. 26]
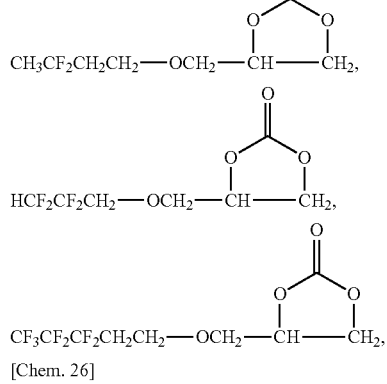
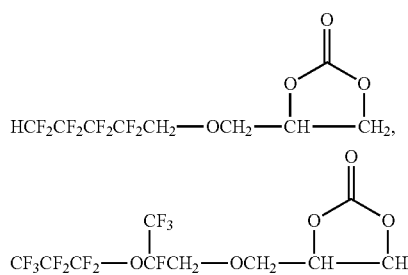
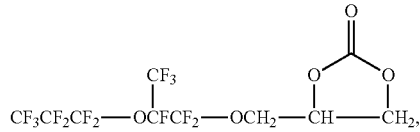
-continued
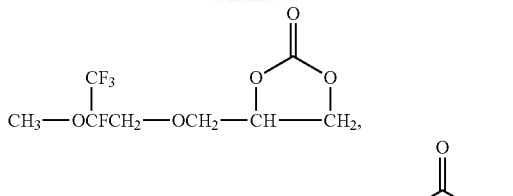
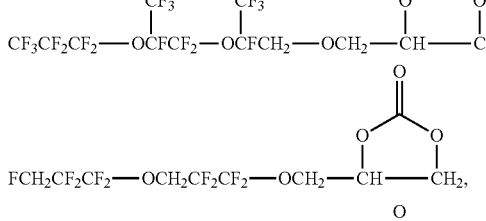
[Chem. 27]
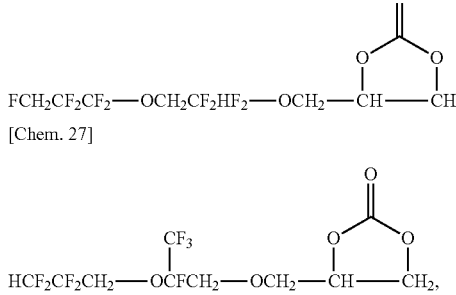
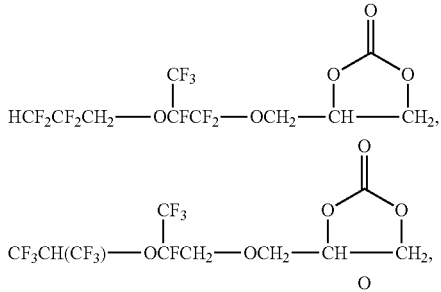
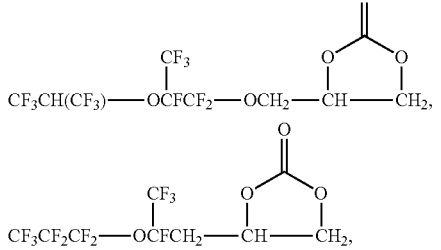
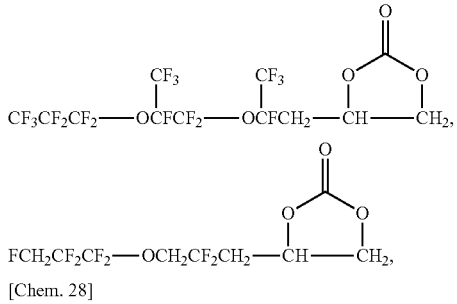
[Chem. 28]
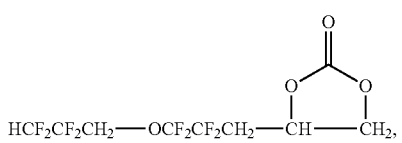

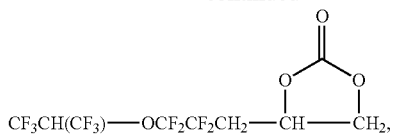
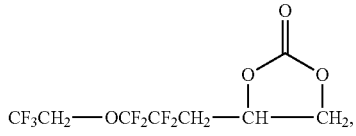
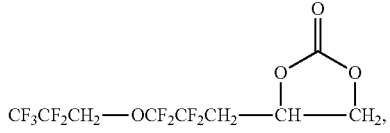
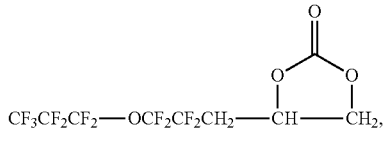
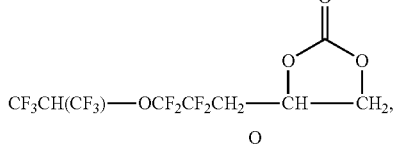
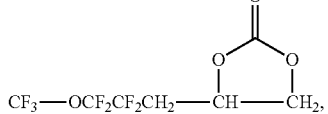
[Chem. 29]
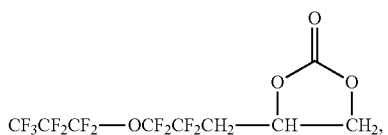
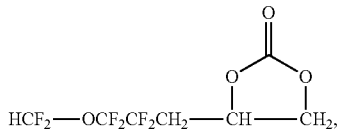
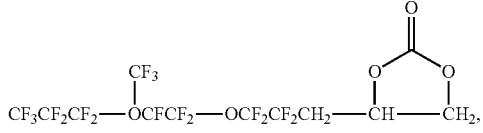
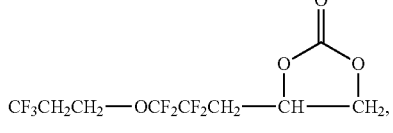
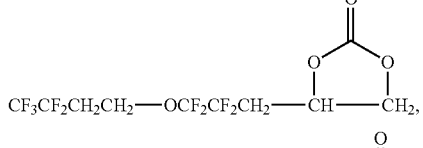
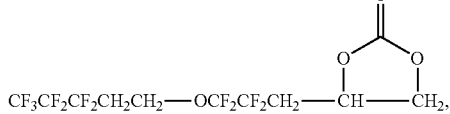
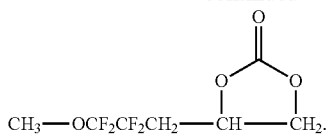
may be mentioned as specific examples of the fluorinated saturated cyclic carbonate in which at least one selected from $X^1$ to $X^4$ is a fluorinated alkyl group (b) containing an ether bond or a fluorinated alkoxy group (c) and the others are —H.
In particular, the fluorinated saturated cyclic carbonate is preferably any of the following compounds.
[Chem. 30]
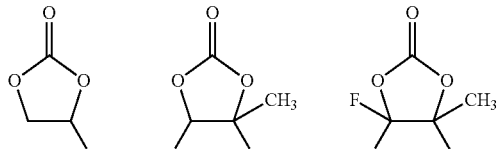
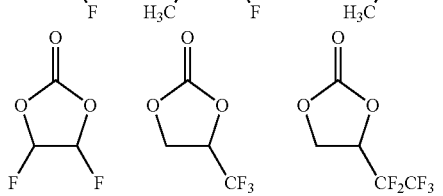
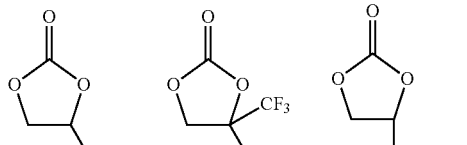
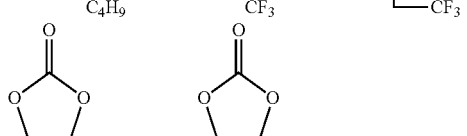
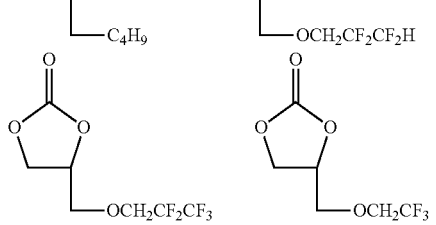
[Chem. 31]
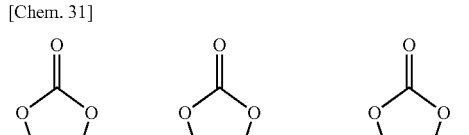
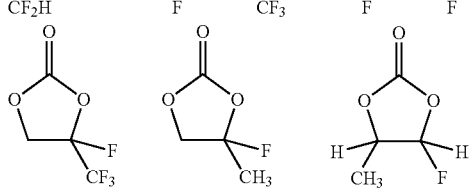

-continued

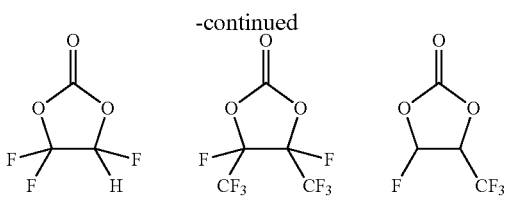

The fluorinated saturated cyclic carbonate more preferably includes at least one selected from the groups consisting of fluoroethylene carbonate, difluoroethylene carbonate, and trifluoromethylethylene carbonate.

Examples of the non-fluorinated acyclic carbonate include hydrocarbon-based acyclic carbonates such as $CH_3OCOOCH_3$ (dimethyl carbonate, DMC), $CH_3CH_2OCOOCH_2CH_3$ (diethyl carbonate, DEC), $CH_3CH_2OCOOCH_3$ (ethyl methyl carbonate, SMC), $CH_3OCOOCH_2CH_2CH_3$ (methyl propyl carbonate), methyl butyl carbonate, ethyl propyl carbonate, and ethyl butyl carbonate. Preferred is at least one selected from the group consisting of ethyl methyl carbonate, diethyl carbonate, and dimethyl carbonate.

An example of the fluorinated acyclic carbonate is a compound represented by the following formula (B):

$$Rf^2OCOOR^6 \quad (B)$$

wherein $Rf^2$ is a C1-C7 fluorinated alkyl group; and $R^6$ is a C1-C7 alkyl group optionally containing a fluorine atom.

In order to be favorably used also at high voltage, the electrolyte solution of the invention preferably contains the fluorinated acyclic carbonate.

$Rf^2$ is a C1-C7 fluorinated alkyl group and $R^6$ is a C1-C7 alkyl group optionally containing a fluorine atom.

The fluorinated alkyl group is an alkyl group in which at least one hydrogen atom thereof is replaced by a fluorine atom. When $R^6$ is an alkyl group containing a fluorine atom, it is a fluorinated alkyl group.

In order to give low viscosity, $Rf^2$ and $R^6$ each preferably have a carbon number of 2 to 7, more preferably 2 to 4.

Too large a carbon number may cause poor low-temperature characteristics and low solubility of an electrolyte salt. Too small a carbon number may cause low solubility of an electrolyte salt, low discharge efficiency, and increased viscosity, for example.

Examples of the fluorinated alkyl group having a carbon number of 1 include $CFH_2—$, $CF_2H—$, and $CF_3—$. In order to give high-temperature storage characteristics, particularly preferred is $CF_2H—$ or $CF_3—$.

In order to give good solubility of an electrolyte salt, preferred examples of the fluorinated alkyl group having a carbon number of 2 or greater include fluorinated alkyl groups represented by the following formula (d-1):

$$R^1—R^2— \quad (d-1)$$

wherein is an alkyl group having a carbon number of 1 or greater and optionally containing a fluorine atom; $R^2$ is a C1-C3 alkylene group optionally containing a fluorine atom; and at least one selected from $R^1$ and $R^2$ contains a fluorine atom.

$R^1$ and $R^2$ each may further contain an atom other than carbon, hydrogen, and fluorine atoms.

$R^1$ is an alkyl group having a carbon number of 1 or greater and optionally containing a fluorine atom. $R^1$ is preferably a C1-C6 linear or branched alkyl group. The carbon number of $R^1$ is more preferably 1 to 6, still more preferably 1 to 3.

Specifically, for example, $CH_3—$, $CH_3CH_2—$, $CH_3CH_2CH_2—$, $CH_3CH_2CH_2CH_2—$, and those represented by the following formulae:

[Chem. 32]

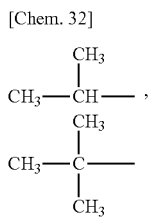

may be mentioned as linear or branched alkyl groups for $R^1$.

Examples of $R^1$ which is a linear alkyl group containing a fluorine atom include $CF_3—$, $CF_3CH_2—$, $CF_3CF_2—$, $CF_3CH_2CH_2—$, $CF_3CF_2CH_2—$, $CF_3CF_2CF_2—$, $CF_3CH_2CF_2—$, $CF_3CH_2CH_2CH_2—$, $CF_3CF_2CH_2CH_2—$, $CF_3CH_2CF_2CH_2—$, $CF_3CF_2CF_2CH_2—$, $CF_3CF_2CF_2CF_2—$, $CF_3CF_2CH_2CF_2—$, $CF_3CH_2CH_2CH_2CH_2—$, $CF_3CF_2CH_2CH_2CH_2—$, $CF_3CH_2CF_2CH_2CH_2—$, $CF_3CF_2CF_2CH_2CH_2—$, $CF_3CF_2CF_2CF_2CH_2—$, $CF_3CF_2CH_2CF_2CH_2—$, $CF_3CF_2CH_2CH_2CH_2CH_2—$, $CF_3CF_2CF_2CF_2CH_2CH_2—$, $CF_3CF_2CH_2CF_2CH_2CH_2—$, $HCF_2—$, $HCF_2CH_2—$, $HCF_2CF_2—$, $HCF_2CH_2CH_2—$, $HCF_2CF_2CH_3—$, $HCF_2CH_2CF_2—$, $HCF_2CF_2CH_2CH_2—$, $HCF_2CH_2CF_2CH_2—$, $HCF_2CF_2CF_2CF_2—$, $HCF_2CF_2CH_2CH_2CH_2—$, $HCF_2CH_2CF_2CH_2CH_2—$, $HCF_2CF_2CF_2CF_2CH_2—$, $HCF_2CF_2CF_2CF_2CH_3CH_2—$, $FCH_2—$, $FCH_2CH_2—$, $FCH_2CF_2—$, $FCH_2CF_2CH_2—$, $FCH_2CF_2CF_2—$, $CH_3CF_2CH_2—$, $CH_3CF_2CF_2—$, $CH_3CF_2CH_2CF_2—$, $CH_3CF_2CF_2CF_2—$, $CH_3CH_2CF_2CF_2—$, $CH_3CF_2CH_3CF_2CH_2—$, $CH_3CF_2CF_2CF_2CH_2—$, $CH_3CF_2CF_2CH_2CH_2—$, $CH_3CH_2CF_2CF_2CH_2—$, $CH_3CF_2CH_2CF_2CH_2—$, $CH_3CF_2CH_2CF_2CH_2CH_2—$, $HCFClCF_2CH_2—$, $HCF_2CFClCH_2—$, $HCF_2CFClCF_2CFClCH_2—$, and $HCFClCF_2CFClCF_2CH_2—$.

Examples of $R^1$ which is a branched alkyl group containing a fluorine atom include those represented by the following formulae.

[Chem. 33]

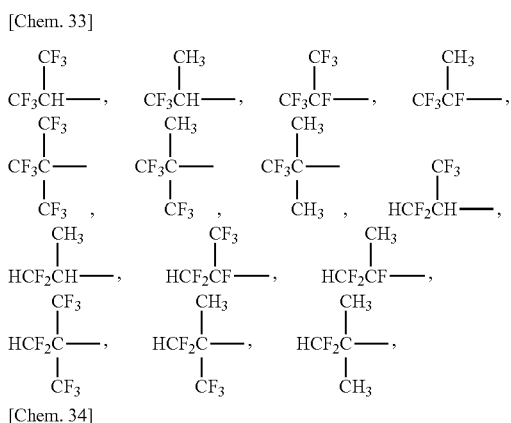

[Chem. 34]

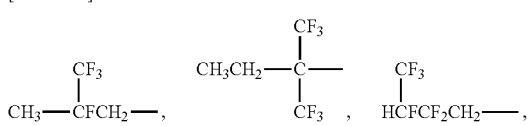

-continued

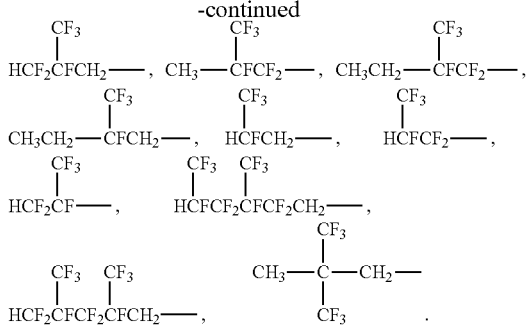

The presence of a branch such as CH$_3$— or CF$_3$— may easily cause high viscosity. Thus, the number of such branches is mere preferably small (one) or zero.

R$^2$ is a C1-C3 alkylene group optionally containing a fluorine atom may be either linear or branched. Examples of a minimum structural unit constituting such a linear or branched alkylene group are shown below, R$^2$ is constituted by one or combination of these units.
(i) Linear Minimum Structural Units
—CH$_2$—, —CHF—, —CF$_2$—, —CHCl—, —CFCl—, —CCl$_2$—
(ii) Branched Minimum Structural Units

[Chem. 35]

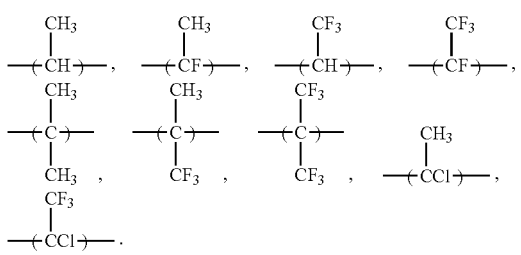

Preferred among these exemplified units are Cl-free structural units because such units may not be dehydrochlorinated by a base, and thus may be more stable.

R$^2$ which is a linear group consists only of any of the above linear minimum structural units, and is preferably —CH$_2$—, —CH$_2$CH$_2$—, or —CF$_2$—. In order to further improve the solubility of an electrolyte salt, —CH$_2$— or —CH$_2$CH$_2$— is more preferred.

R$^2$ which is a branched group includes at least one of the above branched minimum structural units. A preferred example thereof is a group represented by —(CX$^a$X$^b$)— (wherein X$^a$ is H, F, CH$_3$, or CF$_3$; X$^b$ is CH$_3$ or CF$_3$; when X$^b$ is CF$_3$, X$^a$ is H or CH$_3$). Such a group can much further improve the solubility of an electrolyte salt.

For example, CF$_3$CF$_2$—, HCF$_2$CF$_2$—, H$_2$CFCF$_2$—, CH$_3$CF$_2$—, CF$_3$CH$_2$—, CF$_3$CF$_2$CF$_2$—, HCF$_2$CF$_2$CF$_2$—, H$_2$CFCF$_2$CF$_2$—, CH$_3$CF$_2$CF$_2$—, and those represented by the following formulae;

[Chem. 36]

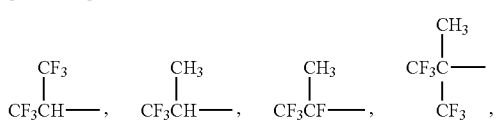

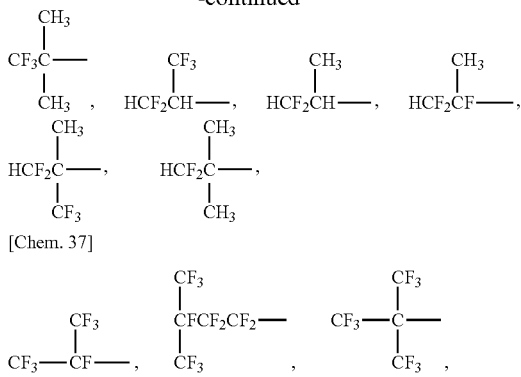

may be mentioned as preferred examples of the fluorinated alkyl group.

The fluorinated alkyl group for Rf$^2$ and R$^6$ is preferably CF$_3$—, CF$_3$CF$_2$—, (CF$_3$)$_2$CH—, CF$_3$CH$_2$—, C$_2$F$_5$CH$_2$—, CF$_3$CF$_2$CH$_2$—, HCF$_2$CF$_2$CH$_2$—, or CF$_3$CFHCF$_2$CH$_2$—. In order to give high incombustibility and good rate characteristics and oxidation resistance, more preferred are CF$_3$CH$_2$—, CF$_3$CF$_2$CH$_2$—, and HCF$_2$CF$_2$CH$_2$—.

R$^6$, when it is an alkyl group free from a fluorine atom, is a C1-C7 alkyl group. In order to give low viscosity, R$^6$ preferably has a carbon number of 1 to 4, more preferably 1 to 3.

Examples of the alkyl group free from a fluorine atom include CH$_3$—, CH$_3$CH$_2$—, (CH$_3$)$_2$CH—, and C$_3$H$_7$—. In order to give low viscosity and good rate characteristics, preferred are CH$_3$— and CH$_3$CH$_2$—.

The fluorinated acyclic carbonate preferably has a fluorine content of 20 to 70% by mass. The fluorinated acyclic carbonate having a fluorine content within the above range can maintain the miscibility with a solvent and the solubility of a salt. The fluorine content is more preferably 30% by mass or more, still more preferably 35% by mass or more, while more preferably 60% by mass or less, still more preferably 50% by mass or less.

In the invention, the fluorine content is a value calculated based on the structural formula of the fluorinated acyclic carbonate by the following formula:

{(Number of fluorine atoms×19)/Molecular weight of fluorinated acyclic carbonate}×100(%).

In order to give low viscosity, the fluorinated acyclic carbonate is preferably any of the following compounds.

[Chem. 38]

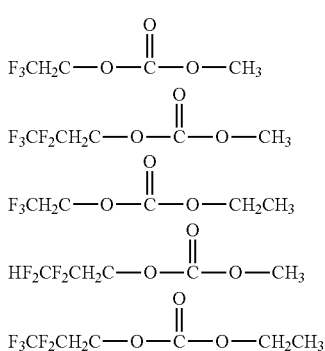

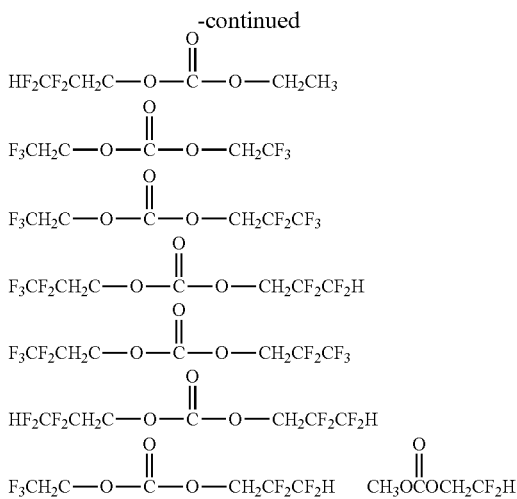

Examples of the non-fluorinated acyclic ester include those containing 3 to 7 carbon atoms in total in the structural formula thereof. Specific examples thereof include methyl acetate, ethyl acetate, n-propyl acetate, isopropyl acetate, n-butyl acetate, isobutyl acetate, t-butyl acetate, methyl propionate, ethyl propionate, n-propyl propionate, isopropyl propionate, n-butyl propionate, isobutyl propionate, t-butyl propionate, methyl butyrate, ethyl butyrate, n-propyl butyrate, isopropyl butyrate, methyl isobutyrate, ethyl isobutyrate, n-propyl isobutyrate, and isopropyl isobutyrate.

In order to improve the ion conductivity owing to reduction in viscosity, preferred among these are methyl acetate, ethyl acetate, n-propyl acetate, n-butyl acetate, methyl propionate, ethyl propionate, n-propyl propionate, isopropyl propionate, methyl butyrate, and ethyl butyrate.

In order to achieve good miscibility with other solvents and to give good oxidation resistance, the fluorinated acyclic ester is preferably a fluorinated acyclic ester represented by the following formula (3):

$$Rf^{31}COORf^{32}$$

wherein $Rf^{31}$ is a C1-C4 fluorinated alkyl group; and $Rf^{32}$ is a C1-C4 alkyl group optionally containing a fluorine atom.

Examples of $Rf^{31}$ include $HCF_2-$, $CF_3-$, $CF_3CF_2-$, $HCF_2CF_2-$, $CH_3CF_2-$, and $CF_3CH_2-$. In order to achieve good viscosity and oxidation resistance, particularly preferred are $HCF_2-$, $CF_3-$, $CF_3CF_2-$, and $CF_3CH_2-$.

Examples of $Rf^{32}$ include $CH_3-$, $C_2H_5-$, $CF_3-$, $CF_3CF_2-$, $(CF_3)_2CH-$, $CF_3CH_2-$, $CF_3CH_2CH_2-$, $CF_3CFHCF_2CH_2-$, $C_2F_5CH_2-$, $CF_2HCF_2CH_2-$, $C_2F_5CH_2CH_2-$, $CF_3CF_2CH_2-$, and $CF_3CF_2CF_2CH_2-$. In order to achieve good miscibility with other solvents, particularly preferred are $CH_3-$, $C_2H_5-$, $CF_3CH_2-$, and $CF_3CH_2CH_2-$.

Specific examples of the fluorinated acyclic ester include one or two or more of $CF_3CH_2C(=O)OCH_3$, $HCF_2C(=O)OCH_3$, $CF_3C(=O)OCH_2CH_2CF_3$, $CF_3C(=O)OCH_2C_2F_5$, $CF_3C(=O)OCH_2CF_2CF_2H$, $CF_3C(=O)OCH_2CF_3$, and $CF_3C(=O)OCH(CF_3)_2$. In order to achieve good miscibility with other solvents and to give rate characteristics, particularly preferred among these are $CF_3CH_2C(=O)OCH_3$, $HCF_2C(=O)OCH_3$, $CF_3C(=O)OCH_2C_2F_5$, $CF_3C(=O)OCH_2CF_2CF_2H$, $CF_3C(=O)OCH_2CF_3$, and $CF_3C(=O)OCH(CF_3)_2$.

In order to reduce an increase in resistance even after high-temperature storage as well as to give a lower resistance than that before the storage, the electrolyte solution of the invention may preferably further contain vinylene carbonate.

The vinylene carbonate is preferably present in an amount of 0.001 to 10% by mass, more preferably 0.01% by mass or more, still more preferably 0.1% by mass or more, while more preferably 5% by mass or less, still more preferably 1% by mass or less, relative to the solvent.

The electrolyte solution of the invention preferably contains an electrolyte salt.

Examples of the electrolyte salt used include alkali metal salts, alkaline earth metal salts, metal salts with aluminum serving as a cation, and ammonium salts, as well as any of those to be used for an electrolyte solution such as liquid salts (ionic liquids), inorganic polymer salts, and organic polymer salts.

The electrolyte salt of the electrolyte solution for a lithium-ion secondary battery is preferably an alkali metal salt, more preferably a lithium salt.

Any lithium salt may be used. Specific examples thereof include the following:

inorganic lithium salts such as $LiPF_6$, $LiBF_4$, $LiClO_4$, $LiAlF_4$, $LiSbF_6$, $LiTaF_6$, and $LiWF_7$;

lithium fluorophosphates such as $LiPO_3F$ and $LiPO_2F_2$;

lithium tungstates such as $LiWOF_5$;

lithium carboxylates such as $HCO_2Li$, $CH_3CO_2Li$, $CH_2FCO_2Li$, $CHF_2CO_2Li$, $CF_3CO_2Li$, $CF_3CH_2CO_2Li$, $CF_3CF_2CO_2Li$, $CF_3CF_2CF_2CO_2Li$, and $CF_3CF_2CF_2CF_2CO_2Li$;

lithium sulfonates such as $FSO_3Li$, $CH_3SO_3Li$, $CH_2FSO_3Li$, $CHF_2SO_3Li$, $CF_3SO_3Li$, $CF_3CF_2SO_3Li$, $CF_3CF_2CF_2SO_3Li$, and $CF_3CF_2CF_2CF_2SO_3Li$;

lithium imide salts such as $LiN(FCO)_2$, $LiN(FCO)(FSO_2)$, $LiN(FSO_2)_2$, $LiN(FSO_2)(CF_3SO_2)$, $LiN(CF_3SO_2)_2$, $LiN(C_2F_5SO_2)_2$, lithium cyclic 1,2-perfluoroethanedisulfonylimide, lithium cyclic 1,3-perfluoropropanedisulfonylimide, and $LiN(CF_3SO_2)(C_4F_9SO_2)$;

lithium methide salts such as $LiC(FSO_2)_3$, $LiC(CF_3SO_2)_3$, and $LiC(C_2F_6SO_2)_3$;

lithium oxalatoborates such as lithium difluorooxalatoborate and lithium bis(oxalate)borate;

lithium oxalatophosphates such as lithium tetrafluorooxalatophosphate, lithium difluorobis(oxalate)phosphate, and lithium tris(oxalate)phosphate; and fluorine-containing organic lithium salts such as salts represented by the formula: $LiPF_a(C_nF_{2n+1})_{6-a}$ (wherein a is an integer of 0 to 5; and n is an integer of 1 to 6) (e.g., $LiPF_4(CF_3)_2$, $LiPF_4(C_2F_5)_2$, $LiPF_4(CF_3SO_2)_2$, $LiPF_4(C_2F_5SO_2)_2$, $LiBF_3CF_3$, $LiBF_3C_2F_5$, $LiBF_3C_3F_7$, $LiBF_2(CF_3)_2$, $LiBF_2(C_2F_5)_2$, $LiBF_2(CF_3SO_2)_2$, and $LiBF_2(C_2F_5SO_2)_2$.

Preferred among these salts is at least one selected from the group consisting of $LiPF_6$, $LiBF_4$, $LiSbF_6$, $LiTaF_6$, $LiPO_2F_2$, $FSO_3Li$, $CF_3SO_3Li$, $LiN(FSO_2)_2$, $LiN(FSO_2)(CF_3SO_2)$, $LiN(CF_3SO_2)_2$, $LiN(C_2F_5SO_2)_2$, lithium cyclic 1,2-perfluoroethanedisulfonylimide, lithium cyclic 1,3-perfluoropropanedisulfonylimide, $LiC(FSO_2)_3$, $LiC(CF_3SO_2)_3$, $LiC(C_2F_5SO_2)_3$, lithium bis(oxalate)borate, lithium difluorooxalatoborate, lithium tetrafluorooxalatophosphate, lithium difluorobis(oxalate)phosphate, $LiBF_3CF_3$, $LiBF_3C_2F_5$, and salts represented by the formula: $LiPF_a(C_nF_{2n+1})_{6-a}$ (wherein a is an integer of 0 to 5; and n is an integer of 1 to 6).

Examples of the salts represented by the formula: $LiPF_a(C_nF_{2n+1})_{6-a}$ include $LiPF_3(CF_3)_3$, $LiPF_3(C_2F_5)_3$, $LiPF_3(C_3F_7)_3$, $LiPF_3(C_4F_9)_3$, $LiPF_4(CF_3)_2$, $LiPF_4(C_2F_5)_2$, $LiPF_4(C_3F_7)_2$, and $LiPF_4(C_4F_9)_2$ (each alkyl group represented by $C_3F_7$ or $C_4F_9$ in the formulae may have either a linear structure or a branched structure).

These lithium salts may be used alone or in combination of two or more, in combination use of two or more thereof, preferred examples thereof include a combination of $LiPF_6$ and $LiBF_4$, a combination of $LiPF_6$ and $FSO_3Li$, and a combination of $LiPF_6$ and $LiPO_2F_2$, each of which have an effect of improving the load characteristics and the cycle characteristics.

Preferred among these are a combination use of $LiPF_6$ and $FSO_3Li$ and of $LiPF_6$ and $LiPO_2F_2$ because the effects thereof are significant. Particularly preferred among these is a combination use of $LiPF_6$ and $LiPO_2F_2$ because it can lead to significant effects even when added in slight amounts.

In the case of a combination use of $LiPF_6$ and $LiBF_4$ or of $LiPF_6$ and $FSO_3Li$, $LiBF_4$ or $FSO_3Li$ may be used in any amount that does not significantly impair the effects of the invention in 100% by mass of the whole electrolyte solution. The amount thereof is usually 0.01% by mass or more, preferably 0.1% by mass or more, while the upper limit thereof is usually 30% by mass or less, preferably 20% by mass or less, relative to the electrolyte solution.

In another example, an inorganic lithium salt and an organic lithium salt are used in combination. Such a combination has an effect of reducing deterioration due to high-temperature storage.

The organic lithium salt is preferably $CF_3SO_3Li$, $LiN(FSO_2)_2$, $LiN(FSO_2)(CF_3SO_2)$, $LiN(CF_3SO_2)_2$, $LiN(C_2F_5SO_2)_2$, lithium cyclic 1,2-perfluoroethanedisulfonylimide, lithium cyclic 1,3-perfluoropropanedisulfonylimide, $LiC(FSO_2)_3$, $LiC(CF_3SO_2)_3$, $LiC(C_2F_5SO_2)_3$, lithium bis(oxalate)borate, lithium difluorooxalatoborate, lithium tetrafluorooxalatophosphate, lithium difluorobis(oxalato)phosphate, $LiBF_3CF_3$, $LiBF_3C_2F_5$, $LiPF_3(CF_3)_3$, $LiPF_3(C_2F_5)_3$, or the like.

In this case, the proportion of the organic lithium salt is preferably 0.1% by mass or more, particularly preferably 0.5% by mass or more, while preferably 30% by mass or less, particularly preferably 20% by mass or less, in 100% by mass of the whole electrolyte solution.

The lithium salt in the electrolyte solution may have any concentration that does not impair the effects of the invention.

In order to make the electric conductivity of the electrolyte solution within a favorable range and to ensure good battery performance, the lithium in the electrolyte solution preferably has a total mole concentration of 0.3 mol/L or higher, more preferably 0.4 mol/L or higher, still more preferably 0.5 mol/L or higher, while preferably 3 mol/L or lower, more preferably 2.5 mol/L or lower, still more preferably 2.0 mol/L or lower.

Too low a total mole concentration of lithium may cause insufficient electric conductivity of the electrolyte solution, while too high a concentration may cause an increase in viscosity and then reduction in electric conductivity, impairing the battery performance.

The electrolyte salt in the electrolyte solution for an electric double layer capacitor is preferably an ammonium salt.

Examples of the ammonium salt include the following salts (IIa) to (IIe).

(IIa) Tetraalkyl Quaternary Ammonium Salts
Preferred examples thereof include tetraalkyl quaternary ammonium salts represented by the following formula (IIa):

[Chem. 39]

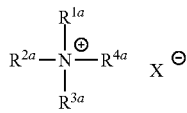

(IIa)

(wherein $R^{1a}$, $R^{2a}$, $R^{3a}$, and $R^{4a}$ are the same as or different from each other, and are each a C1-C6 alkyl group optionally containing an ether bond; and $X^-$ is an anion). In order to improve the oxidation resistance, any or all of the hydrogen atoms in the ammonium salt are also preferably replaced by a fluorine atom and/or a C1-C4 fluorinated alkyl group.

Preferred specific examples thereof include
tetraalkyl quaternary ammonium salts represented by the following formula (IIa-1):

[Chem. 40]

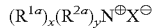

(IIa-1)

(wherein $R^{1a}$, $R^{2a}$, and $X^-$ are defined as described above; x and y are the same as or different from each other, and are each art integer of 0 to 4 with x+y=4), and alkyl ether group-containing trialkyl ammonium salts represented by the following formula (IIa-2);

[Chem. 41]

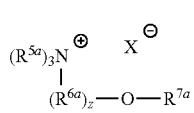

(IIa-2)

(wherein $R^{5a}$ is a C1-C6 alkyl group; $R^{6a}$ is a C1-C6 divalent hydrocarbon group; $R^{7a}$ is a C1-C4 alkyl group; z is 1 or 2; and $X^-$ is art anion). Introduction of an alkyl ether group enables reduction in viscosity.

The anion $X^-$ may be either an inorganic anion or an organic anion. Examples of the inorganic anion include $AlCl_4^-$, $BF_4^-$, $PF_6^-$, $AsF_6^-$, $TaF_6^-$, $I^-$, and $SbF_6^-$. Examples of the organic anion include $CF_3COO^-$, $CF_3SO_3^-$, $(CF_3SO_2)_2N^-$, and $(C_2F_5SO_2)_2N^-$.

In order to achieve good oxidation resistance and ionic dissociation, $BF_4^-$, $PF_6^-$, $AsF_6^-$, and $SbF_6^-$ are preferred.

Preferred specific examples of the tetraalkyl quaternary ammonium salts to be used include $Et_4NBF_4$, $Et_4NClO_4$, $Et_4NPF_6$, $Et_4NAsF_6$, $Et_4NSbF_6$, $Et_4NCF_3SO_3$, $Et_4N(CF_3SO_2)_2N$, $Et_4NC_4F_9SO_3$, $Et_3MeNBF_4$, $Et_3MeNClO_4$, $Et_3MeNPF_6$, $Et_3MeNAsF_6$, $Et_3MeNSbF_6$, $Et_3MeNCF_3SO_3$, $Et_3MeN(CF_3SO_2)_2N$, $Et_3MeNC_4F_9SO_3$, and N,N-diethyl-N-methyl-N-(2-methoxyethyl)ammonium salts. In particular, $Et_4NBF_4$, $Et_4NPF_6$, $Et_4SbF_6$, $Et_4NAsF_6$, $Et_3MeNBF_4$, and an N,N-diethyl-N-methyl-N-(2-methoxyethyl)ammonium salt may be mentioned as examples.

(IIb) Spirocyclic Bipyrrolidinium Salts
Preferred examples thereof include
spirocyclic bipyrrolidinium salts represented by the following formula (IIb-1):

[Chem. 42]

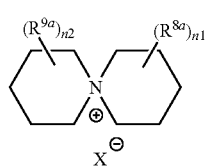

(IIb-1)

(wherein $R^{8a}$ and $R^{9a}$ are the same as or different from each other, and are each a C1-C4 alkyl group; $X^-$ is an anion; n1 is an integer of 0 to 5 and n2 is an integer of 0 to 5), spirocyclic bipyrrolidinium salts represented by the following formula (IIb-2):

[Chem. 43]

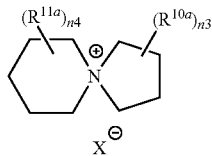

(IIb-2)

(wherein $R^{10a}$ and $R^{11a}$ are the same as or different from each other, and are each a C1-C4 alkyl group $X^-$ is an anion n3 is an integer of 0 to 5; and n4 is an integer of 0 to 5), and spirocyclic bipyrrolidinium salts represented by the following formula (IIb-3):

[Chem. 44]

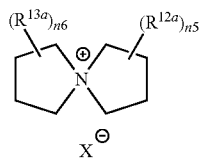

(IIb-3)

(wherein $R^{12a}$ and $R^{13a}$ are the same as or different from each other, and are each a C1-C4 alkyl group; $X^-$ is an anion; n5 is an integer of 0 to 5; and n6 is an integer of 0 to 5). In order to improve the oxidation resistance, any or all of the hydrogen atoms in the spirocyclic bipyrrolidinium salt are also preferably replaced by a fluorine atom and/or a C1-C4 fluorinated alkyl group.

Preferred specific examples of the anion $X^-$ are the same as those mentioned for the salts (IIa). In order to achieve good dissociation and a low internal resistance under high voltage, $BF_4^-$, $PF_6^-$, $(CF_3SO_2)_2N^-$, or $(C_2F_5SO_2)_2N^-$ is particularly preferred.

For example, those represented by the following formulae:

[Chem. 45]

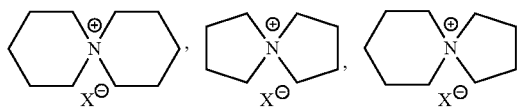

may be mentioned as preferred specific examples of the spirocyclic bipyrrolidinium salts.

These spirocyclic bipyrrolidinium salts are excellent, in solubility in a solvent, oxidation resistance, and ion conductivity.

(IIc) Imidazolium Salts

Preferred examples thereof include imidazolium salts represented by the following formula (IIc):

[Chem. 46]

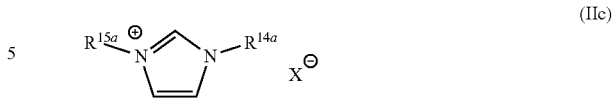

(IIc)

wherein $R^{14a}$ and $R^{15a}$ are the same as or different from each other, and are each a C1-C6 alkyl group; and $X^-$ is an anion.

In order to improve the oxidation resistance, any or all of the hydrogen atoms in the imidazolium salt are also preferably replaced by a fluorine atom and/or a C1-C4 fluorinated alkyl group.

Preferred specific examples of the anion $X^-$ are the same as those mentioned for the salts (IIa).

For example, one represented by the following formula:

[Chem. 47]

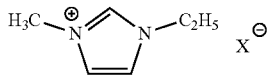

may be mentioned as a preferred specific example thereof.

This imidazolium salt is excellent in that it has low viscosity and good solubility.

(IId) N-alkylpyridinium Salts

Preferred examples thereof include N-alkylpyridinium salts represented by the following formula (IId);

[Chem. 48]

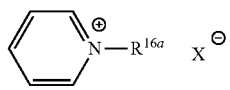

(IId)

wherein $R^{16a}$ is a C1-C6 alkyl group; and $X^-$ is an anion.

In order to improve the oxidation resistance, any or all of the hydrogen atoms in the N-alkylpyridinium salt are also preferably replaced by a fluorine atom and/or a C1-C4 fluorinated alkyl group.

Preferred specific examples of the anion $X^-$ are the same as those mentioned for the salts (IIa).

For example, those represented by the following formulae:

[Chem. 49]

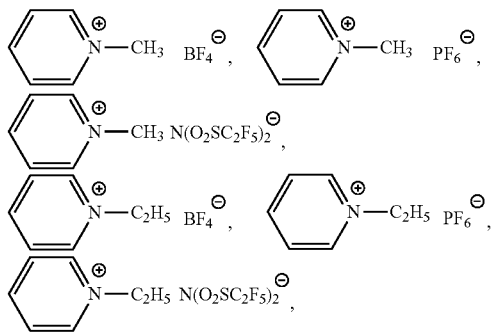

may be mentioned as preferred specific examples thereof.

These N-alkylpyridinium salts are excellent in that they have low viscosity and good solubility.

(IIe) N,N-dialkylpyrrolidinium Salts

Preferred examples thereof include N,N-dialkylpyrrolidinium salts represented by the following formula (IIe);

[Chem. 50]

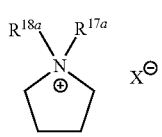

(IIe)

wherein $R^{17a}$ and $R^{18a}$ are the same as or different from each other, and are each a C1-C6 alkyl group; and $X^-$ is an anion.

In order to improve the oxidation resistance, any or all of the hydrogen atoms in the N,N-dialkylpyrrolidinium salt are also preferably replaced by a fluorine atom and/or a C1-C4 fluorinated alkyl group, Preferred specific examples of the anion $X^-$ are the same as those mentioned for the salts (IIa).

For example, those represented by the following formulae:

[Chem. 51]

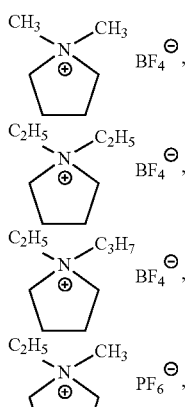

[Chem. 52]

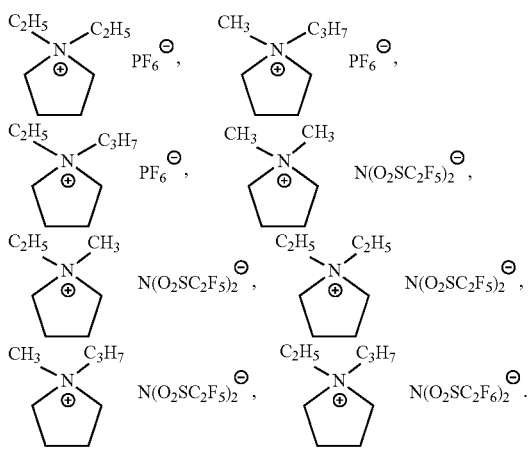

may be mentioned as preferred specific examples thereof.

These N,N-dialkylpyrrolidinium salts are excellent in that they have low viscosity and good solubility.

Preferred among these ammonium salts are those represented by the formula (IIa), (IIb), or (IIe) because they can have good solubility, oxidation resistance, and ion conductivity. More preferred are those represented by the following formulae:

[Chem. 53]

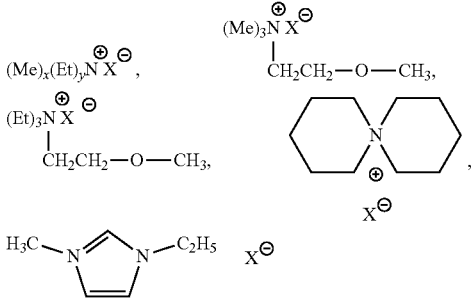

wherein Me is a methyl group; Et is an ethyl group; and $X^-$, x, and y are defined as in the formula (IIa-1).

A lithium salt may be used as an electrolyte salt for an electric double layer capacitor. Preferred examples thereof include $LiPF_6$, $LiBF_4$, $LiAsF_6$, $LiSbF_6$, and $LiN(SO_2C_2H_5)_2$.

In order to further increase the capacity, a magnesium salt may be used. Preferred examples of the magnesium salt include $Mg(ClO_4)_2$ and $Mg(OOC_2H_5)_2$.

The ammonium salt serving as an electrolyte salt is preferably used at a concentration of 0.6 mol/L or higher. The ammonium salt at a concentration lower than 0.6 mol/L may cause not only poor low-temperature characteristics but also high initial internal resistance. The concentration of the electrolyte salt is more preferably 0.9 mol/L or higher.

In order to give good low-temperature characteristics, the concentration is preferably 3.0 mol/L or lower, more preferably 2 mol/L or lower.

In order to give excellent low-temperature characteristics, the concentration is preferably 0.3 to 1.9 mol/L when the ammonium salt is triethyl methyl ammonium tetrafluoroborate ($TEMABF_4$).

The concentration is preferably 0.7 to 2.0 mol/L when the ammonium salt is spirobipyrrolidinium tetrafluoroborate ($SBPBF_4$).

The electrolyte solution of the invention preferably contains a polyethylene oxide that has a weight average molecular weight of 2000 to 4000 and has —OH, —OCOOH, or —COOH at an end.

The presence of such a compound can improve the stability at the interfaces with the respective electrodes, improving the characteristics of an electrochemical device.

Examples of the polyethylene oxide include polyethylene oxide monool, polyethylene oxide carboxylate, polyethylene oxide diol, polyethylene oxide dicarbaxylate, polyethylene oxide triol, and polyethylene oxide tricarboxylate. These may be used alone or in combination of two or more.

In order to give better characteristics of an electrochemical device, preferred are a mixture of polyethylene oxide monool and polyethylene oxide diol and a mixture of polyethylene oxide carboxylate and polyethylene oxide dicarboxylate.

The polyethylene oxide having too small a weight average molecular weight may be easily oxidatively decomposed. The weight average molecular weight is more preferably 3000 to 4000.

The weight average molecular weight can be determined by gel permeation chromatography (GPC) in polystyrene equivalent.

The polyethylene oxide is preferably present in an amount of $1\times10^{-6}$ to $1\times10^{-2}$ mol/kg in the electrolyte solution. Too large an amount of the polyethylene oxide may cause poor characteristics of an electrochemical device.

The amount of the polyethylene oxide is more preferably $5\times10^{-6}$ mol/kg or more.

The electrolyte solution of the invention may further contain any of other components such as an unsaturated cyclic carbonate, an overcharge inhibitor, and a known different aid. This can reduce impairment of the characteristics of an electrochemical device.

The unsaturated cyclic carbonate is a cyclic carbonate containing an unsaturated bond, i.e., a cyclic carbonate that contains at least one carbon-carbon unsaturated bond in the molecule. Examples of the unsaturated cyclic carbonate include vinylene carbonate derivatives other than vinylene carbonate, ethylene carbonate derivatives substituted with a substituent that contains an aromatic ring, a carbon-carbon double bond, or a carbon-carbon triple bond, phenyl carbonate derivatives, vinyl carbonate derivatives, allyl carbonate derivatives, and catechol carbonate derivatives.

Examples of the vinylene carbonate derivatives other than vinylene carbonate include methylvinylene carbonate, 4,5-dimethylvinylene carbonate, 4,5-diethylvinylene carbonate, phenylvinylene carbonate, 4,5-diphenylvinylene carbonate, vinyivinylene carbonate, 4,5-divinylvinylene carbonate, allylvinylene carbonate, 4,5-diallylvinylene carbonate, 4-fluorovinylene carbonate, 4-fluoro-5-methylvinylene carbonate, 4-fluoro-5-phenylvinylene carbonate, 4-fluoro-5-vinyivinylene carbonate, and 4-allyl-5-fluorovinylene carbonate.

Specific examples of the ethylene carbonate derivatives substituted with a substituent that contains an aromatic ring, a carbon-carbon double bond, or a carbon-carbon triple bond include vinylethylene carbonate, 4,5-divinylethylene carbonate, 4-methyl-5-vinylethylene carbonate, 4-allyl-5-vinylethylene carbonate, ethynylethylene carbonate, 4,5-diethynylethylene carbonate, 4-methyl-5-ethynylethylene carbonate, 4-vinyl-5-ethynylethylene carbonate, 4-allyl-5-ethynylethylene carbonate, phenylethylene carbonate, 4,5-diphenylethylene carbonate, 4-phenyl-5-vinylethylene carbonate, 4-allyl-5-phenylethylene carbonate, allylethylene carbonate, 4,5-diallylethylene carbonate, and 4-methyl-5-allylethylene carbonate.

The unsaturated cyclic carbonate is preferably methylvinylene carbonate, 4,5-dimethylvinylene carbonate, vinylvinylene carbonate, 4,5-vinylvinylene carbonate, allylvinylene carbonate, 4,5-diallylvinylene carbonate, vinylethylene: carbonate, 4,5-divinylethylene carbonate, 4-methyl-5-vinylethylene carbonate, allylethylene carbonate, 4,5-diallylethylene carbonate, 4-methyl-5-allylethylene carbonate, 4-allyl-5-vinylethylene carbonate, ethynylethylene carbonate, 4,5-diethynylethylene carbonate, 4-methyl-5-ethynylethylene carbonate, and 4-vinyl-5-ethynylethylene carbonate. In order to form a more stable interface protecting film, particularly preferred are vinylethylene carbonate and ethynylethylene carbonate.

The unsaturated cyclic carbonate may have any molecular weight that does not significantly impair the effects of the invention. The molecular weight is preferably 50 or higher and 250 or lower. The unsaturated cyclic carbonate having a molecular weight within this range can easily ensure its solubility in the electrolyte solution and can easily lead to sufficient achievement of the effects of the invention. The molecular weight of the unsaturated cyclic carbonate is more preferably 80 or higher, while more preferably 150 or lower.

The unsaturated cyclic carbonate may be produced by any production method, and may be produced by a known method selected as appropriate.

The unsaturated cyclic carbonates may be used alone or in any combination of two or more at any ratio.

The unsaturated cyclic carbonate may be contained in any amount that does not significantly impair the effects of the invention. The amount of the unsaturated cyclic carbonate is preferably 0.001% by mass or more, more preferably 0.01% by mass or more, still more preferably 0.1% by mass or more, of 100% by mass of the solvent in the invention. The amount is preferably 5% by mass or less, more preferably 4% by mass or less, still more preferably 3% by mass or less. The unsaturated cyclic carbonate in an amount within the above range allows an electrochemical device containing the electrolyte solution to easily exhibit a sufficient effect of improving the cycle characteristics, and can easily avoid a situation with impaired high-temperature storage characteristics, generation of a large amount of gas, and a reduced discharge capacity retention.

In addition to the aforementioned non-fluorinated unsaturated cyclic carbonates, a fluorinated unsaturated cyclic carbonate may also suitably be used, as an unsaturated cyclic carbonate. The fluorinated unsaturated cyclic carbonate is a cyclic carbonate containing an unsaturated bond and a fluorine atom.

The number of fluorine atoms in the fluorinated unsaturated cyclic carbonate may be any number that is 1 or greater. The number of fluorine atoms is usually 6 or smaller, preferably 4 or smaller, most preferably 1 or 2.

Examples of the fluorinated unsaturated cyclic carbonate include fluorinated vinylene carbonate derivatives, and fluorinated ethylene carbonate derivatives substituted with a substituent that, contains an aromatic ring or a carbon-carbon double bond.

Examples of the fluorinated vinylene carbonate derivatives include 4-fluorovinylene carbonate, 4-fluoro-5-methylvinylene carbonate, 4-fluoro-5-phenylvinylene carbonate, 4-allyl-5-fluorovinylene carbonate, and 4-fluoro-5-vinyivinylene carbonate.

Examples of the fluorinated ethylene carbonate derivatives substituted with a substituent that contains an aromatic ring or a carbon-carbon double bond include 4-fluoro-4-vinylethylene carbonate, 4-fluoro-4-allylethylene carbonate, 4-fluoro-5-vinylethylene carbonate, 4-fluoro-5-allylethylene carbonate, 4,4-difluoro-4-vinylethylene carbonate, 4,4-difluoro-4-allylethylene carbonate, 4,5-difluoro-4-vinylethylene carbonate, 4,5-difluoro-4-allylethylene carbonate, 4-fluoro-4,5-divinyl ethylene carbonate, 4-fluoro-4,5-diallylethylene carbonate, 4,5-difluoro-4,5-divinylethylene carbonate, 4,5-difluoro-4,5-diallylethylene carbonate, 4-fluoro-4-phenylethylene carbonate, 4-fluoro-5-phenylethylene carbonate, 4,4-difluoro-5-phenylethylene carbonate, and 4,5-difluoro-4-phenylethylene carbonate.

In order to form a stable interface protecting film, more preferred as the fluorinated unsaturated cyclic carbonate are 4-fluorovinylene carbonate, 4-fluoro-5-methylvinylene carbonate, 4-fluoro-5-vinyivinylene carbonate, 4-allyl-5-fluorovinylene carbonate, 4-fluoro-4-vinylethylene carbonate, 4-fluoro-4-allylethylene carbonate, 4-fluoro-5-vinylethylene carbonate, 4-fluoro-5-allylethylene carbonate, 4,4-difluoro-4-vinylethylene carbonate, 4,4-difluoro-4-allylethylene carbonate, 4,5-difluoro-4-vinylethylene carbonate, 4,5-difluoro-4-allylethylene carbonate, 4-fluoro-4,5-divinylethylene carbonate, 4-fluoro-4,5-diallylethylene carbonate, 4,5-difluoro-4,5-divinylethylene carbonate, and 4,5-difluoro-4,5-diallylethylene carbonate.

The fluorinated unsaturated cyclic carbonate may have any molecular weight that does not significantly impair the effects of the invention. The molecular weight is preferably 50 or higher and 500 or lower. The fluorinated unsaturated cyclic carbonate having a molecular weight within this range can easily ensure the solubility of the fluorinated unsaturated cyclic carbonate in the electrolyte solution and enables easy achievement of the effects of the invention.

The fluorinated unsaturated cyclic carbonate may be produced by any method, and may be produced by any known method selected as appropriate. The molecular weight is more preferably 100 or higher and more preferably 200 or lower.

The fluorinated unsaturated cyclic carbonates may be used alone or in any combination of two or more at any ratio.

The fluorinated unsaturated cyclic carbonate may be contained in any amount that does not significantly impair the effects of the invention.

The amount of the fluorinated unsaturated cyclic carbonate is usually preferably 0.01% by mass or more, more preferably 0.1% by mass or more, still more preferably 0.5% by mass or more, while preferably 5% by mass or less, more preferably 3% by mass or less, still more preferably 2% by mass or less, of 100% by mass of the electrolyte solution.

The fluorinated unsaturated cyclic carbonate in an amount within this range allows an electrochemical, device containing the electrolyte solution to exhibit an effect of sufficiently improving the cycle characteristics and can easily avoid a situation with reduced high-temperature storage characteristics, generation of a large amount of gas, and a reduced discharge capacity retention.

In order to effectively reduce burst or combustion of a battery in case of overcharge, for example, of an electrochemical device containing the electrolyte solution, the electrolyte solution of the invention may contain an overcharge inhibitor.

Examples of the overcharge inhibitor include aromatic compounds such as biphenyl, alkyl biphenyl, terphenyl, partially hydrogenated terphenyl, cyclohexyl benzene, t-butyl benzene, t-amyl benzene, diphenyl ether, and dibenzofuran; partially fluorinated aromatic compounds such as 2-fluorobiphenyl, o-cyclohexyl fluorobenzene, and p-cyclohexyl fluorobenzene; and fluoroanisole compounds such as 2,4-difluoroanisole, 2,5-difluoroanisole, 2,6-difluoroanisole, and 3,5-difluoroanisole.

Preferred are aromatic compounds such as biphenyl, alkyl biphenyl, terphenyl, partially hydrogenated terphenyl, cyclohexyl benzene, t-butyl benzene, t-amyl benzene, diphenyl ether, and dibenzofuran.

These compounds may be used alone or in combination of two or more.

In order to achieve good balance between the overcharge inhibiting characteristics and the high-temperature storage characteristics with a combination use of two or more compounds, preferred is a combination of cyclohexyl benzene and t-butyl benzene or t-amyl benzene, or a combination of at least one oxygen-free aromatic compound selected from biphenyl, alkyl biphenyl, terphenyl, partially hydrogenated terphenyl, cyclohexyl benzene, t-butyl benzene, t-amyl benzene, and the like and at least one oxygen-containing aromatic compound selected from diphenyl ether, dibenzofuran, and the like.

The electrolyte solution of the invention may further contain a known different aid.

Examples of the different, aid include carbonate compounds such as erythritan carbonate, spiro-bis-dimethylene carbonate, and methoxyethyl-methyl carbonate; carboxylic anhydrides such as succinic anhydride, glutaric anhydride, maleic anhydride, citraconic anhydride, glutaconic anhydride, itaconic anhydride, diglycolic anhydride, cyclohexanedicarboxylic anhydride, cyclopentanetetracarboxylic dianhydride, and phenylsuccinic anhydride; spiro compounds such as 2,4,8,10-tetraoxaspiro[5.5]undecane and 3,9-divinyl-2,4,8,10-tetraoxaspiro[5.5]undecane; sulfur-containing compounds such as ethylene sulfite, 1,3-propanesultone, 1-fluoro-1,3-propanesultone, 2-fluoro-1,3-propanesultone, 3-fluoro-1,3-propanesultone, 1-propane-1,3-sultone, 1-fluoro-1-propene-1,3-sultone, 2-fluoro-1-propene-1,3-sultone, 3-fluoro-1-propene-1,3-sultone, 1,4-butanesultone, 1-butene-1,4-sultone, 3-butene-1,4-sultone, methyl fluorosulfonate, ethyl fluorosulfonate, methyl methanesulfonate, ethyl methanesulfonate, busulfan, sulfolene, diphenyl sulfone, N,N-dimethylmethanesulfonamide, N,N-diethylmethanesulfonamide, methyl vinyl sulfonate, ethyl vinyl sulfonate, allyl vinyl sulfonate, propargyl vinyl sulfonate, methyl allyl sulfonate, ethyl allyl sulfonate, allyl allyl sulfonate, propargyl allyl sulfonate, and 1,2-bis(vinylsulfonyloxy)ethane; nitrogen-containing compounds such as 1-methyl-2-pyrrolidinone, 1-methyl-2-piperidone, 3-methyl-2-oxazolidinone, 1,3-dimethyl-2-imidazolidinone, and N-methylsuccinimide; phosphorus-containing compounds such as trimethyl phosphite, triethyl phosphite, triphenyl phosphite, trimethyl phosphate, triethyl phosphate, triphenyl phosphate, dimethyl methyl phosphonate, diethyl ethyl phosphonate, dimethyl vinyl phosphonate, diethyl vinyl phosphonate, ethyl diethyl phosphonoacetate, methyl dimethyl phosphinate, ethyl diethyl phosphinate, trimethylphosphine oxide, and triethylphosphine oxide; hydrocarbon compounds such as heptane, octane, nonane, decane, and cycloheptane; and fluorine-containing aromatic compounds such as fluorobenzene, difluorobenzene, hexafluorobenzene, and benzotrifluoride.

These compounds may be used alone or in combination of two or more.

These aids can improve the capacity retention characteristics and the cycle characteristics after high-temperature storage.

The different aid may be used in any amount that does not significantly impair the effects of the invention.

The amount of the different aid is preferably 0.01% by mass or more and 5% by mass or less of 100% by mass of the electrolyte solution.

The different aid in an amount within this range can easily sufficiently exhibit the effects thereof and can easily avoid a situation with reduction in battery characteristics such as high-load discharge characteristics.

The amount of the different aid is more preferably 0.1% by mass or more, still more preferably 0.2% by mass or more, while more preferably 3% by mass or less, still more preferably 1% by mass or less.

The electrolyte solution of the invention may contain an acid anhydride having a succinic acid skeleton. Examples of the acid anhydride having a succinic acid skeleton include succinic anhydride, maleic anhydride, citraconic acid, 2-methylsuccinic acid, 2,3-dimethylsuccinic acid, 2-fluorosuccinic acid, and 2,3-difluorosuccinic acid. Preferred among these is succinic anhydride or maleic anhydride.

The acid anhydride having a succinic acid skeleton is preferably present in an amount of 0.1 to 10% by mass, more preferably 0.5% by mass or more, while more preferably 5% by mass or less, in the electrolyte solution.

The electrolyte solution of the invention may contain a cyclic sulfonic acid compound. Examples of the cyclic sulfonic acid compound include 1,3-propanesultone, 1,4-butanesultone, 1-fluoro-1,3-propanesultone, 2-fluoro-1,3-propanesultone, and 3-fluoro-1,3-propanesultone. In order to improve the high-temperature characteristics, the electrolyte solution of the invention preferably contains 1,3-propanesultone and/or 1,4-butanesultone.

The amount of the cyclic sulfonic acid compound is preferably 0.1 to 10% by mass, more preferably 0.5% by mass or more, while more preferably 5% by mass or less, in the electrolyte solution.

The electrolyte solution of the invention may further contain any of a cyclic carboxylate, an ether compound, a nitrogen-containing compound, a boron-containing compound, an organosilicon-containing compound, a fireproof agent (flame retardant), a surfactant, an additive for increasing the permittivity, and an improver for cycle characteristics and rate characteristics, to the extent that does not impair the effects of the invention.

Examples of the cyclic carboxylate include those having a carbon number of 3 to 12 in total in the structural formula. Specific examples thereof include gamma-butyrolactone, gamma-valerolactone, gamma-caprolactone, and epsilon-caprolactone. In order to improve the characteristics of an electrochemical device owing to improvement in the degree of dissociation of lithium ions, particularly preferred is gamma-butyrolactone.

In general, the cyclic carboxylate is preferably present in an amount of 0.1% by mass or more, more preferably 1% by mass or more, of 100% by mass of the solvent. The cyclic carboxylate in an amount within this range can easily improve the electric conductivity of the electrolyte solution, improving the large-current discharge characteristics of an electrochemical device. The amount of the cyclic carboxylate is also preferably 10% by mass or less, more preferably 5% by mass or less. Such an upper limit may allow the electrolyte solution to have a viscosity within an appropriate range, may make it possible to avoid a reduction in the electric conductivity, may reduce an increase in the resistance of the negative electrode, and may allow the electrochemical device to have large-current discharge characteristics within a favorable range.

The cyclic carboxylate to be suitably used may also be a fluorinated cyclic carboxylate (fluorine-containing lactone). Examples of the fluorine-containing lactone include fluorine-containing lactones represented by the following formula (E):

[Chem. 54]

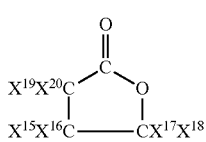
(E)

wherein $X^{15}$ to $X^{20}$ are the same as or different from each other, and are each —B, —F, —Cl, —CH$_3$, or a fluorinated alkyl group; and at least one selected from $X^{15}$ to $X^{20}$ is a fluorinated alkyl group.

Examples of the fluorinated alkyl group for $X^{15}$ to $X^{20}$ include —CFH$_2$, —CF$_2$H, —CF$_3$, —CH$_2$CF$_3$, —CF$_2$CF$_3$, —CH$_2$CF$_2$CF$_3$, and —CF(CF$_3$)$_2$. In order to achieve high oxidation resistance and an effect of improving the safety, —CH$_2$CF$_3$ and —CH$_2$CF$_2$CF$_3$ are preferred.

One of $X^{15}$ to $X^{20}$ or a plurality thereof may be replaced by —H, —F, —Cl, —CH$_3$, or a fluorinated alkyl group only when at least one selected from $X^{15}$ to $X^{20}$ is a fluorinated alkyl group. In order to give good solubility of an electrolyte salt, the number of substituents is preferably 1 to 3, more preferably 1 or 2.

The substitution of the fluorinated alkyl group may be at any of the above sites. In order to give a good synthesizing yield, the substitution site is preferably $X^{17}$ and/or $X^{18}$. In particular, $X^{17}$ or $X^{18}$ is preferably a fluorinated alkyl group, especially —CH$_2$CF$_3$ or —CH$_2$CF$_2$CF$_3$. The substituent for $X^{15}$ to $X^{20}$ other than the fluorinated alkyl group is —H, —F, —Cl, or CH$_3$. In order to give good solubility of an electrolyte salt, —H is preferred.

In addition to those represented by the above; formula, the fluorine-containing lactone may also be a fluorine-containing lactone represented by the following formula (F):

[Chem. 55]

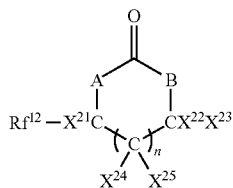
(F)

wherein one of A or B is $CX^{26}X^{27}$ (where $X^{26}$ and $X^{27}$ are the same as or different from each other, and are each —H, —F, —Cl, —CF$_3$, —CH$_3$, or an alkylene group in which a hydrogen atom is optionally replaced by a halogen atom and which optionally contains a hetero atom in the chain) and the other is an oxygen atom; Rf$^{12}$ is a fluorinated alkyl group or fluorinated alkoxy group optionally containing an ether bond; $X^{21}$ and $X^{22}$ are the same as or different from each other, and are each —H, —F, —Cl, —CF$_3$, or CH$_3$; $X^{23}$ to $X^{23}$ are the same as or different from each other, and are each —H, —F, —Cl, or an alkyl group in which a hydrogen atom is optionally replaced, by a halogen atom and which optionally contains a hetero atom in the chain; and n=0 or 1.

A preferred example of the fluorine-containing lactone represented by the formula (F) is a 5-membered ring structure represented by the following formula (G):

[Chem. 56]

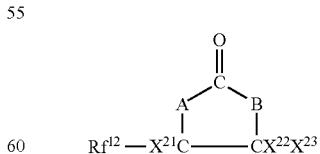
(G)

(wherein A, B, Rf$^{12}$, $X^{21}$, $X^{22}$, and $X^{23}$ are defined as in the formula (F)) because it can be easily synthesized and can have good chemical stability. Further, in relation to the combination of A and B, fluorine-containing lactones represented by the following formula (H);

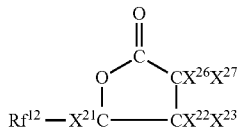

(H)

(wherein $Rf^{12}$, $X^{21}$, $X^{22}$, $X^{23}$, $X^{26}$, and $X^{27}$ are defined as in the formula (F)) and fluorine-containing lactones represented by the following formula (I):

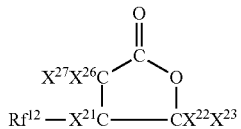

(I)

(wherein $Rf^{12}$, $X^{21}$, $X^{22}$, $X^{23}$, $X^{26}$, and $X^{27}$ are defined as in the formula (F)) may be mentioned.

In order to particularly give excellent characteristics such as high permittivity and high withstand voltage, and to improve the characteristics of the electrolyte solution in the invention, for example, to give good solubility of an electrolyte salt and to reduce the internal resistance well, those represented by the following formulae:

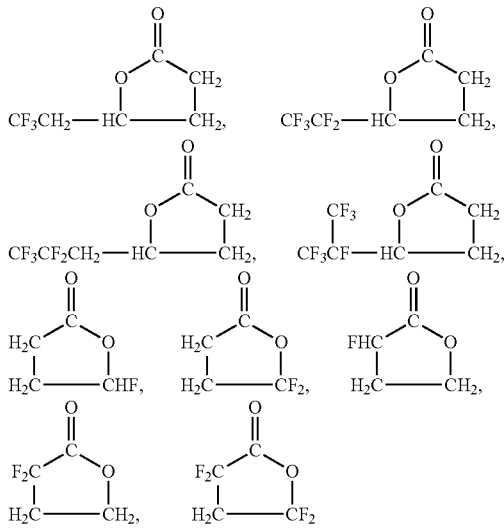

may be mentioned.

The presence of a fluorinated cyclic carboxylate can lead to, for example, effects of improving the ion conductivity, improving the safety, and improving the stability at high temperature.

The ether compound is preferably a C3-C10 acyclic ether or a C3-C6 cyclic ether.

Examples of the C3-C10 acyclic ether include diethyl ether, di-n-butyl ether, dimethoxymethane, methoxyethoxymethane, diethoxymethane, dimethoxyethane, methoxyethoxyethane, diethoxyethane, ethylene glycol di-n-propyl ether, ethylene glycol di-n-butyl ether, and diethylene glycol dimethyl ether.

Further, the ether compound may also suitably be a fluorinated ether.

An example of the fluorinated ether is a fluorinated ether (K) represented by the following formula (K):

(K)

(wherein $Rf^1$ and $Rf^2$ are the same as or different from each other, and are each a C1-C10 alkyl group or a C1-C10 fluorinated alkyl group; and at least one selected from. $Rf^1$ and $Rf^2$ is a fluorinated alkyl group). The presence of the fluorinated ether (K) allows the electrolyte solution to have improved Incombustibility as well as improved stability and safety at high temperature under high voltage.

In the formula (K), at least one selected from $Rf^1$ and $Rf^2$ is a C1-C10 fluorinated alkyl group. In order to allow the electrolyte solution to have further improved incombustibility and further improved stability and safety at high temperature under high voltage, both $Rf^1$ and $Rf^2$ are preferably C1-C10 fluorinated alkyl groups. In this case, $Rf^1$ and $Rf^2$ may be the same as or different from each other.

Particularly preferably, $Rf^1$ and $Rf^2$ are the same as or different from each other, and $Rf^1$ is a C3-C6 fluorinated alkyl group and $Rf^2$ is a C2-C6 fluorinated alkyl group.

If the sum of the carbon numbers of $Rf^1$ and $Rf^2$ is too small, the fluorinated ether may have too low a boiling point. Too large a carbon number of $Rf^1$ or $Rf^2$ may cause low solubility of an electrolyte salt, may start to adversely affect the miscibility with other solvents, and may cause high viscosity, resulting in poor rate characteristics. In order to achieve an excellent boiling point and rate characteristics, advantageously, the carbon number of $Rf^1$ is 3 or 4 and the carbon number of $Rf^2$ is 2 or 3.

The fluorinated ether (K) preferably has a fluorine content of 40 to 75% by mass. The fluorinated ether (K) having a fluorine content within this range may lead to particularly excellent balance between the non-flammability and the miscibility. The above range is also preferred for good oxidation resistance and safety.

The lower limit of the fluorine content is more preferably 45% by mass, still more preferably 50% by mass, particularly preferably 55% by mass. The upper limit thereof is more preferably 70% by mass, still more preferably 66% by mass.

The fluorine content of the fluorinated ether (K) is a value calculated based on the structural formula of the fluorinated ether (K) by the following formula:

{(Number of fluorine atoms×19)/(Molecular weight of fluorinated ether (K))}×100(%).

Examples of $Rf^1$ include $CF_3CF_2CH_2$—, $CF_3CFHCF_2$—, $HCF_2CF_2CF_2$—, $HCF_2CF_2CH_2$—, $CF_3CF_2CH_2CH_2$—, $CF_3CFHCF_2CH_2$—, $HCF_2CF_2CF_2CF_2$—, $HCF_2CF_2CF_2CH_2$—, $HCF_2CF_2CH_2CH_2$—, and $HCF_2CF(CF_3)CH_2$—.

Examples of $Rf^2$ include $CF_3CF_2CH_2$—, $CF_3CFHCF_2$—, $CF_2HCF_2CF_2$—, $CF_2HCF_2CH_2$—, $CF_3CF_2CH_2CH_2$—, $CF_3CFHCF_2CH_2$—, $CF_2HCF_2CF_2CF_2$—, $CF_2HCF_2CF_2CH_2$—, $CF_2HCF_2CH_2CH_2$—, $CF_2HCF(CF_3)CH_2$—, $CF_2HCF_2$—, $CF_2HCH_2$—, and $CH_3CF_2$—.

Specific examples of the fluorinated ether (K) include $HCF_2CF_2CH_2OCF_2CF_2H$, $CF_3CF_2CH_2OCF_2CF_2H$, $HCF_2CF_2CH_2OCF_2CFHCF_3$, $CF_3CF_2CH_2OCF_2CFHCF_3$, $C_6F_{13}OCH_3$, $C_6F_{13}OC_2H_5$, $C_8F_{17}OCH_3$, $C_8F_{17}OC_2H_5$, $CF_3CFHCF_2CH(CH_3)OCF_2CFHCF_3$, $HCF_2CF_2OCH(C_2H_5)_2$, $HCF_2CF_2OC_4H_9$, $HCF_2CF_2OCH_2CH(C_2H_5)_2$, and $HCF_2CF_2OCH_2CH(CH_3)_2$.

In particular, those having $HCF_2$— or $CF_3CFH$— at one or each end can provide a fluorinated ether (K) having excellent polarizability and a high boiling point. The boiling point of the fluorinated ether (K) is preferably 67° C. to 120° C., more preferably 80° C. or higher, still more preferably 90° C. or higher.

Such a fluorinated ether (K) may include one or two or more of $CF_3CH_2OCF_2CFHCF_3$, $CF_3CF_2CH_2OCF_2CFHCF_3$, $HCF_2CF_2CH_2OCF_2CFHCF_3$, $HCF_2CF_2CH_2OCH_2CF_2CF_2H$, $CF_3CFHCF_2CH_2OCF_2CFHCF_3$, $HCF_2CF_2CH_2OCF_2CF_2H$, $CF_3CF_2CH_2OCF_2CF_2H$, and the like.

Advantageously, in order to achieve a high boiling-point and good miscibility with other solvents and to give good solubility of an electrolyte salt, the fluorinated ether (K) is preferably at least one selected from the group consisting of $HCF_2CF_2CH_2OCF_2CFHCF_3$ (boiling point: 106° C.), $CF_3CF_2CH_2OCF_2CFHCF_3$ (boiling point: 82° C.), $HCF_2CF_2CH_2OCF_2CF_2H$ (boiling point: 92° C.), and $CF_3CF_2CH_2OCF_2CF_2H$ (boiling point: 68° C.), more preferably at least one selected from the group consisting of $HCF_2CF_2CH_2OCF_2CFHCF_3$ (boiling point: 106° C.), and $HCF_2CF_2CH_2OCF_2CF_2H$ (boiling point; 92° C.).

Examples of the C3-C6 cyclic ether include 1,3-dioxane, 2-methyl-1,3-dioxane, 4-methyl-1,3-dioxane, 1,4-dioxane, and fluorinated compounds thereof. In order to achieve a high ability to solvate with lithium ions and improve the degree of ion dissociation, preferred are dimethoxymethane, diethoxymethane, ethoxymethoxymethane, ethylene glycol n-propyl ether, ethylene glycol di-n-butyl ether, and diethylene glycol dimethyl ether. In order to achieve low viscosity and to give a high ion conductivity, particularly preferred are dimethoxymethane, diethoxymethane, and ethoxymethoxymethane.

Examples of the nitrogen-containing compound include nitrile, fluorine-containing nitrile, carboxylic acid amide, fluorine-containing carboxylic acid amide, sulfonic acid amide, and fluorine-containing sulfonic acid amide. Also, 1-methyl-2-pyrrolidinone, 1-methyl-2-piperidone, 3-methyl-2-oxazilidinone, 1,3-dimethyl-2-imidazoiidinone, and N-methylsuccinimide may be used.

Examples of the boron-containing compound include borates such as trimethyl borate and triethyl borate, boric acid ethers, and alkyl borates.

Examples of the organosilicon-containing compound include $(CH_3)_4$—Si and $(CH_3)_3$—Si—$Si(CH_3)_3$.

Examples of the fireproof agent (flame retardant) include organophosphates and phosphazene-based compounds. Examples of the organophosphates include fluorine-containing alkyl phosphates, non-fluorine-containing alkyl phosphates, and aryl phosphates. In order to achieve a flame retardant effect even in a small amount, fluorine-containing alkyl phosphates are particularly preferred.

Specific examples of the fluorine-containing alkyl phosphates include fluorine-containing dialkyl phosphates disclosed in JP H11-233141 A, cyclic alkyl phosphates disclosed in JP H11-283669 A, and fluorine-containing trialkyl phosphates.

Preferred examples of the fireproof agent (flame retardant) include $(CH_3O)_3P=O$, $(CF_3CH_2O)_3P=O$, $(HCF_2CH_2O)_3P=O$, $(CF_3CF_2CH_2)_3P=O$, and $(HCF_2CF_2CH_2)_3P=O$.

The surfactant may be any of cationic surfactants, anionic surfactants, nonionic surfactants, and amphoteric surfactants. In order to give good cycle characteristics and rate characteristics, the surfactant is preferably one containing a fluorine atom.

Preferred examples of such a surfactant containing a fluorine atom include fluorine-containing carboxylic acid salts represented by the following formula:

(wherein $Rf^1$ is a C3-C10 fluorinated alkyl group optionally containing an ether bond; $M^+$ is $Li^+$, $Na^+$, $K^+$, or $NHR'_3{}^+$, wherein R's are the same as or different from each other, and are each H or a C1-C3 alkyl group), and fluorine-containing sulfonic acid salts represented by the following formula:

(wherein $Rf^2$ is a C3-C10 fluorinated alkyl group optionally containing an ether bond; $M^+$ is $Li^+$, $Na^+$, $K^+$, or $NHR'_3{}^+$, wherein R's are the same as or different from each other, and are each H or a C1-C3 alkyl group).

In order to reduce the surface tension of the electrolyte solution without impairing the charge and discharge cycle characteristics, the surfactant is preferably present in an amount of 0.01 to 2% by mass in the electrolyte solution.

Examples of the additive for increasing the permittivity include sulfolane, methyl sulfolane, γ-butyrolactone, γ-valerolactone, acetonitrile, and propionitrile.

Examples of the improver for cycle characteristics and rate characteristics include methyl acetate, ethyl acetate, tetrahydrofuran, and 1,4-dioxane.

The electrolyte solution of the invention may be combined with a polymer material and thereby formed into a gel-like (plasticized), gel electrolyte solution.

Examples of such a polymer material include conventionally known polyethylene oxide and polypropylene oxide, and modified products thereof (see JP H08-222270 A, JP 2002-100405 A); polyacrylate-based polymers, polyacrylonitrile, and fluororesins such as polyvinylidene fluoride and vinylidene fluoride-hexafluoropropylene copolymers (see JP H04-506726 T, JP H08-507407 T, JP H10-294131 A); and composites of any of these fluororesins and any hydrocarbon resin (see JP H11-35765 A, JP H11-86630 A). In particular, polyvinylidene fluoride or a vinylidene fluoride-hexafluoropropylene copolymer is preferably used as a polymer material for a gel electrolyte.

The electrolyte solution of the invention may also contain an ion conductive compound disclosed in Japanese Patent Application No. 2004-301934.

This ion conductive compound is an amorphous fluorine-containing polyether compound having a fluorine-containing group at a side chain and is represented by the following formula (1-1):

wherein D is represented by the following formula (2-1):

[wherein D1 is an ether unit containing a fluorine-containing ether group at a side chain and is represented by the following formula (2a):

[Chem. 60]

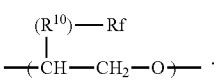

(wherein Rf is a fluorine-containing ether group optionally containing a crosslinkable functional group; and $R^{10}$ is a group or a bond that links Rf and the main chain);

FAE is an ether unit containing a fluorinated alkyl group at a side chain and is represented by the following formula (2b):

[Chem. 61]

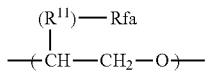
$$-\!(\!CH\!-\!CH_2\!-\!O\!)\!- \quad (2b)$$

(wherein Rfa is a hydrogen atom or a fluorinated alkyl group optionally containing a crosslinkable functional group; and $R^{12}$ is a group or a bond that links Rfa and the main chain);

AE is an ether unit represented by the following formula (2c):

[Chem. 62]

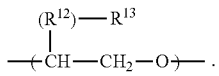
$$-\!(\!CH\!-\!CH_2\!-\!O\!)\!- \,. \quad (2c)$$

(wherein $R^{13}$ is a hydrogen atom, an alkyl group optionally containing a crosslinkable functional group, an aliphatic cyclic hydrocarbon group optionally containing a crosslinkable functional group, or an aromatic hydrocarbon group optionally containing a crosslinkable functional group; and $R^{12}$ is a group or a bond that links $R^{13}$ and the main chain);

Y is a unit containing at least one selected from the following formulae (2d-1) to (2d-3):

[Chem. 63]

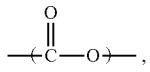
(2d-1)

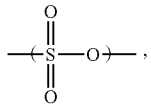
(2d-2)

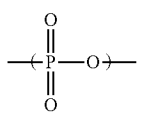
(2d-3)

n is an integer of 0 to 200;
m is an integer of 0 to 200;
p is an integer of 0 to 10000;
q is an integer of 1 to 100;
n+m is not 0; and
the bonding order of D1, FAE, AE, and Y is not specified]; and A and B are the same as or different from each other, and are each a hydrogen atom, an alkyl group optionally containing a fluorine atom and/or a crosslinkable functional group, a phenyl group optionally containing a fluorine atom and/or a crosslinkable functional group, a —COOH group, —OR (where R is a hydrogen atom or an alkyl group optionally containing a fluorine atom and/or a crosslinkable functional group), an ester group, or a carbonate group, and when an end of D is an oxygen atom, A and B are each none of a —COOH group, —OR, an ester group, and a carbonate group.

The electrolyte solution of the invention may further contain a different additive, if necessary. Examples of the different additive include metal oxides and glass.

The electrolyte solution of the invention preferably contains 0.5 to 70 ppm of HF. The presence of HF can promote formation of a film of the additive. Too small an amount of HF tends to impair the ability of the additive to form a film on the negative electrode, impairing the characteristics of an electrochemical device. Too large an amount of HF tends to impair the oxidation resistance of the electrolyte solution due to the influence by HF. The electrolyte solution of the invention, even when containing HF in an amount within the above range, causes no reduction in capacity recovery in high-temperature storage of an electrochemical device.

The amount of HF is more preferably 1 ppm or more, still more preferably 2.5 ppm or more. The amount of HF is also more preferably 60 ppm or less, still more preferably 50 ppm or less, particularly preferably 30 ppm or less.

The amount of HF can be determined by neutralization titration.

The electrolyte solution of the invention is preferably prepared by any method using the aforementioned components.

The electrolyte solution of the invention can be suitably applied to electrochemical devices such as secondary batteries, lithium-ion secondary batteries, and electric double layer capacitors. Such an electrochemical device including the electrolyte solution ox the invention is also one aspect of the invention.

Examples of the electrochemical devices include lithium-ion secondary batteries, capacitors (electric double-layer capacitors), radical batteries, solar cells (in particular, dye-sensitized solar cells), fuel cells, various electrochemical sensors, electrochromic elements, electrochemical switching elements, aluminum electrolytic capacitors, and tantalum electrolytic capacitors. Preferred are lithium-ion secondary batteries and electric double-layer capacitors.

A module including the electrochemical device is also one aspect of the invention.

The invention also relates to a secondary battery including the electrolyte solution of the invention. The secondary battery may be a lithium ion secondary battery. The following describes an exemplary case in which the electrochemical device or the secondary battery of the invention is a lithium ion secondary battery or an electric double-layer capacitor.

The lithium-ion secondary battery may include a positive electrode, a negative electrode, and the above electrolyte solution.

<Positive Electrode>

The positive electrode includes a positive electrode active material layer containing a positive electrode active material and a current collector.

The positive electrode active material may be any material that can electrochemically occlude and release lithium ions. For example, a substance containing lithium and at least one transition metal is preferred. Specific examples thereof include lithium-containing transition metal complex oxides and lithium-containing transition metal phosphoric acid compounds. In particular, the positive electrode active material is preferably a lithium-containing transition metal complex oxide that generates high voltage.

The transition metal of the lithium-containing transition metal complex oxide is preferably V, Ti, Cr, Mn, Fe, Co, Ni, Cu, or the like. Specific examples thereof include lithium-cobalt complex oxides such as $LiCoO_2$, lithium-nickel complex oxides such as $LiNiO_2$, lithium-manganese complex oxides such as $LiMnO_2$, $LiMn_2O_4$, and $Li_2MnO_4$, and those obtained by substituting some of transition metal atoms as main components of these lithium transition metal complex oxides with another element such as Na, K, B, F, Al, Ti, V, Cr, Mn, Fe, Co, Li, Ni, Cu, Zn, Mg, Ga, Zr, Si, Kb, Mo, Sn, or W. Specific examples of those obtained by substitution include $LiNi_{0.5}Mn_{0.5}O_2$, $LiNi_{0.85}Co_{0.10}Al_{0.05}O_2$, $LiNi_{0.5}Co_{0.2}Mn_{0.3}O_2$m $LiNi_{0.6}Co_{0.2}Mn_{0.2}O_2$, $LiNi_{0.33}Co_{0.33}Mn_{0.33}O_2$, $LiNi_{0.45}Co_{0.10}Al_{0.45}O_2$, $LiMn_{1.8}Al_{0.2}O_4$, and $LiMn_{1.5}Ni_{0.5}O_4$.

The lithium-containing transition metal complex oxide is preferably any of $LiMn_{1.5}Ni_{0.5}O_4$, $LiNi_{0.5}Co_{0.2}Mn_{0.3}O_2$, and $LiNi_{0.6}Co_{0.2}Mn_{0.2}O_2$ each of which has a high energy density even, at high voltage.

The transition metal of the lithium-containing transition metal phosphoric acid compound is preferably V, Ti, Cr, Mn, Fe, Co, Ni, Cu, or the like. Specific examples thereof include iron phosphates such as $LiFePO_4$, $Li_3Fe_2(PO_4)_3$, and $LiFeP_2O_7$, cobalt phosphates such as $LiCoPO_4$, and those obtained by substituting some of transition metal atoms as main components of these lithium transition metal phosphoric acid compounds with another element such as Al, Ti, V, Cr, Mn, Fe, Co, Li, Ni, Cu, Zn, Mg, Ga, Zr, Nb, or Si.

Examples of the lithium-containing transition metal complex oxide include lithium-manganese spinel complex oxides represented by the formula: $Li_aMn_{2-b}M^1_bO_4$ (wherein $0.9 \le a$; $0 \le b \le 1.5$; and $M^1$ is at least one metal selected from the group consisting of Fe, Co, Ni, Cu, Zn, Al, Sn, Cr, V, Ti, Mg, Ca, Sr, B, Ga, In, Si, and Ge), lithium-nickel complex oxides represented by the formula: $LiNi_{1-c}M^2_cO_2$ (wherein $0 \le c \le 0.5$; and $M^2$ is at least one metal selected from the group consisting of Fe, Co, Mn, Cu, Zn, Al, Sn, Cr, V, Ti, Mg, Ca, Sr, B, Ga, In, Si, and Ge), and lithium-cobalt complex oxides represented by the formula: $LiCo_{1-d}M^3_dO_2$ (wherein $0 \le d \le 0.5$; and $M^3$ is at least one metal selected from the group consisting of Fe, Ni, Mn, Cu, Zn, Al, Sn, Cr, V, Ti, Mg, Ca, Sr, B, Ga, In, Si, and Ge).

In order to provide a high-power lithium-ion secondary battery having a high energy density, preferred is $LiCoO_2$, $LiMnO_2$, $LiNiO_2$, $LiMn_2O_4$, $LiNi_{0.8}Co_{0.15}Al_{0.05}O_2$, or $LiNi_{1/3}CO_{1/3}Mn_{1/3}O_2$.

Other examples of the positive electrode active material include $LiFePO_4$, $LiNi_{0.8}Co_{0.2}O_2$, $Li_{1.2}Fe_{0.4}Mn_{0.4}O_2$, $LiNi_{0.5}Mn_{0.5}O_2$, and $LiV_3O_6$.

In order to improve the continuous charge characteristics, the positive electrode active material preferably contains lithium phosphate. Lithium phosphate may be used in any manner, and is preferably used in admixture with the positive electrode active material. The lower limit of the amount of lithium phosphate used is preferably 0.1% by mass or more, more preferably 0.3% by mass or more, still more preferably 0.5% by mass or more, relative to the sum of the amounts of the positive electrode active material and lithium phosphate. The upper limit thereof is preferably 10% by mass or less, more preferably 8% by mass or less, still more preferably 5% by mass or less.

To a surface of the positive electrode active material may be attached a substance having a composition different from the positive electrode active material. Examples of the substance attached to the surface include oxides such as aluminum oxide, silicon oxide, titanium oxide, zirconium oxide, magnesium oxide, calcium oxide, boron oxide, antimony oxide, and bismuth oxide; sulfates such as lithium sulfate, sodium sulfate, potassium sulfate, magnesium sulfate, calcium sulfate, and aluminum sulfate; carbonates such as lithium carbonate, calcium carbonate, and magnesium carbonate; and carbon.

Such a substance may be attached to a surface of the positive electrode active material by, for example, a method of dissolving or suspending the substance in a solvent, impregnating the solution or suspension into the positive electrode active material, and drying the impregnated material; a method of dissolving or suspending a precursor of the substance in a solvent, impregnating the solution or suspension into the positive electrode active material, and heating the material and the precursor to cause a reaction therebetween; or a method of adding the substance to a precursor of the positive electrode active material and simultaneously sintering the materials. In the case of attaching carbon, for example, a carbonaceous material in the form of activated carbon may be mechanically attached to the surface afterward.

For the amount of the substance attached to the surface in terms of the mass relative to the amount of the positive electrode active material, the lower limit thereof is preferably 0.1 ppm or more, more preferably 1 ppm or more, still more preferably 10 ppm or more, while the upper limit thereof is preferably 20% or less, more preferably 10% or less, still more preferably 5% or less. The substance attached to the surface can reduce oxidation of the electrolyte solution on the surface of the positive electrode active material, improving the battery life. Too small an amount of the substance may fail to sufficiently provide this effect. Too large an amount thereof may hinder the entrance and exit of lithium ions, increasing the resistance.

Particles of the positive electrode active material may have any shape conventionally used, such as a bulky shape, a polyhedral shape, a spherical shape, an ellipsoidal shape, a plate shape, a needle shape, or a pillar shape. The primary particles may agglomerate to form secondary particles.

The positive electrode active material has a tap density of preferably 0.5 g/cm³ or higher, more preferably 0.8 g/cm³ or higher, still more preferably 1.0 g/cm³ or higher. The positive electrode active material having a tap density below the lower limit may cause an increased amount of a dispersion medium required and increased amounts of a conductive material and a binder required in formation of the positive electrode active material layer, as well as limitation on the packing fraction of the positive electrode active material in the positive electrode active material layer, resulting in limitation on the battery capacity. A complex oxide powder having a high tap density enables formation of a positive electrode active material layer with a high density. The tap density is preferably as high as possible and has no upper limit, in general. Still, too high a tap density may cause diffusion of lithium ions in the positive electrode active material layer with the electrolyte solution serving as a diffusion medium to function as a rate-determining step, easily impairing the load characteristics. Thus, the upper limit of the tap density is preferably 4.0 g/cm³ or lower, more preferably 3.7 g/cm³ or lower, still more preferably 3.5 g/cm³ or lower.

In the invention, the tap density is determined as a powder packing density (tap density) g/cm³ when 5 to 10 g of the positive electrode active material powder is packed into a 10-ml glass graduated cylinder and the cylinder is tapped 200 times with a stroke of about 20 mm.

The particles of the positive electrode active material, have a median size d50 (or a secondary particle size when the primary particles agglomerate to form secondary particles) of preferably 0.3 μm or greater, more preferably 0.5 μm or greater, still more preferably 0.8 μm or greater, most preferably 1.0 μm or greater, while preferably 30 μm or smaller, more preferably 27 μm or smaller, still more preferably 25 μm or smaller, most preferably 22 μm or smaller. The particles having a median size below the lower limit may fail to provide a product with a high tap density. The particles having a median size greater than the upper limit may cause prolonged diffusion of lithium in the particles, impairing the battery performance and generating streaks in formation of the positive electrode for a battery, i.e., when the active material and components such as a conductive material and a binder are formed into slurry by adding a solvent and the slurry is applied in the form of a film, for example. Mixing two or more positive electrode active materials having different median sizes d50 can further improve the easiness of packing in formation of the positive electrode.

In the invention, the median size d50 is determined using a known laser diffraction/scattering particle size distribution analyzer. In the case of using LA-920 (Horiba, Ltd.) as the particle size distribution analyzer, the dispersion medium used in the measurement is a 0.1% by mass sodium hexametaphosphate aqueous solution and the measurement refractive index is set to 1.24 after 5-minute ultrasonic dispersion.

When the primary particles agglomerate to form secondary particles, the average primary particle size of the positive electrode active material is preferably 0.05 μm or greater, more preferably 0.1 μm or greater, still more preferably 0.2 μm or greater. The upper limit thereof is preferably 5 μm or smaller, more preferably 4 μm or smaller, still more preferably 3 μm or smaller, most preferably 2 μm or smaller. The primary particles having an average primary particle size greater than the upper limit may have difficulty in forming spherical secondary particles, adversely affecting the powder packing. Further, such primary particles may have a greatly reduced specific surface area, highly possibly impairing the battery performance such as output characteristics. In contrast, the primary particles having an average primary particle size below the lower limit may usually be insufficiently grown crystals, causing poor charge and discharge reversibility, for example.

In the invention, the primary particle size is measured by scanning electron microscopic (SEM) observation, Specifically, the primary particle size is determined as follows. A photograph at a magnification of 1000× is first taken. Any 50 primary particles are selected and the maximum length between the left and right boundary lines of each primary particle is measured along the horizontal line. Then, the average value of the maximum lengths is calculated, which is defined as the primary particle size.

The positive electrode active material has a BET specific surface area of preferably 0.1 $m^2/g$ or larger, more preferably 0.2 $m^2/g$ or larger, still more preferably 0.3 $m^2/g$ or larger, while preferably 50 $m^2/g$ or smaller, more preferably 40 $m^2/g$ or smaller, still more preferably 30 $m^2/g$ or smaller. The positive electrode active material having a BET specific surface area smaller than the above range may easily impair the battery performance. The positive electrode active material having a BET specific surface area larger than the above range may less easily have an increased tap density, easily causing a difficulty in applying the material in formation of the positive electrode active material layer.

In the invention, the BET specific surface area is defined by a value determined by single point BET nitrogen adsorption utilizing a gas flow method using a surface area analyzer (e.g., fully automatic surface area measurement device, Ohkura Riken Co., Ltd.), a sample pre-dried in nitrogen stream at 150° C. for 30 minutes, and a nitrogen-helium gas mixture with the nitrogen pressure relative to the atmospheric pressure being accurately adjusted to 0.3.

When the lithium-ion secondary battery is used as a large-size lithium-ion secondary battery for hybrid vehicles or distributed generation, it needs to achieve high output. Thus, the particles of the positive electrode active material preferably mainly composed of secondary particles.

The particles of the positive electrode active material preferably include 0.5 to 7.0% by volume of fine particles having an average secondary particle size of 40 μm or smaller and having an average primary particle size of 1 μm or smaller. The presence of fine particles having an average primary particle size of 1 μm or smaller enlarges the contact area with the electrolyte solution and enables more rapid diffusion of lithium ions between the electrode and the electrolyte solution, improving the output performance of the battery.

The positive electrode active material may be produced by any usual method of producing an inorganic compound. In particular, a spherical, or ellipsoidal active material can be produced by various methods. For example, a material substance of transition metal is dissolved or crushed and dispersed in a solvent such as water, and the pH of the solution or dispersion is adjusted under stirring to form a spherical precursor. The precursor is recovered and, if necessary, dried. Then, a Li source such as LiOH, $Li_2CO_3$, or $LiNO_3$ is added thereto and the mixture is sintered at high temperature, thereby providing an active material.

In production of the positive electrode, the aforementioned positive electrode active materials may be used alone or in any combination of two or more thereof having different compositions at any ratio. Preferred examples of the combination in this case include a combination of $LiCoO_2$ and $LiMn_2O_4$ in which part of Mn may optionally be replaced by a different transition metal (e.g., $LiNi_{0.33}Co_{0.33}Mn_{0.33}O_2$), and a combination with $LiCoO_2$ in which part of Co may optionally be replaced by a different transition metal.

In order to achieve a high battery capacity, the amount of the positive electrode active material is preferably 50 to 99% by mass, more preferably 80 to 99% by mass, of the positive electrode mixture. The amount of the positive electrode active material in the positive electrode active material layer is preferably 80% by mass or more, more preferably 82% by mass or more, particularly preferably 84% by mass or more, while preferably 99% by mass or less, more preferably 98% by mass or less. Too small an amount of the positive electrode active material in the positive electrode active material layer may cause an insufficient electric capacity. In contrast, too large an amount thereof may cause insufficient strength of the positive electrode.

The positive electrode mixture preferably further contains a binder, a thickening agent, and a conductive material.

The binder may be any material that is safe against a solvent to be used in production of the electrode and the electrolyte solution. Examples thereof include polyvinylidene fluoride, polytetrafluoroethylene, polyethylene, polypropylene, SBR (styrene-butadiene rubber), isoprene rubber, butadiene rubber, ethylene-acrylic acid copolymers, ethylene-methacrylic acid copolymers, polyethylene terephthalate, polymethyl methacrylate, polyimide, aromatic polyamide, cellulose, nitro cellulose, NBR (acrylonitrile-butadiene rubber), fluoroelastomers, ethylene-propylene rubber, styrene-butadiene-styrene block copolymers and hydrogenated products thereof, EPDM (ethylene-propylene-diene terpolymers), styrene-ethylene-butadiene-ethylene copolymers, styrene-isoprene-styrene block copolymers and hydrogenated products thereof, syndiotactic-1,2-polybutadiene, polyvinyl acetate, ethylene-vinyl acetate copolymers, propylene-α-olefin copolymers, fluorinated polyvinylidene fluoride, tetrafluoroethylene-ethylene copolymers, and polymer compositions having ion conductivity of alkali metal ions (especially, lithium ions). These substances may be used alone or in any combination of two or more at any ratio.

The amount of the binder, which is expressed as the proportion, of the binder in the positive electrode active material layer, is usually 0.1% by mass or more, preferably 1% by mass or more, more preferably 1.5% by mass or more. The proportion is also usually 80% by mass or less, preferably 60% by mass or less, still more preferably 40% by mass or less, most preferably 10% by mass or less. Too low a proportion of the binder may fail to sufficiently hold the positive electrode active material and cause insufficient mechanical strength of the positive electrode, impairing the battery performance such as cycle characteristics. In contrast, too high a proportion thereof may cause reduction in battery capacity and conductivity.

Examples of the thickening agent include carboxymethyl cellulose, methyl cellulose, hydroxymethyl cellulose, ethyl cellulose, polyvinyl alcohol, oxidized starch, monostarch phosphate, casein, and salts thereof. These agents may be used alone or in any combination of two or more at any ratio.

The proportion of the thickening agent relative to the active material is usually 0.1% by mass or higher, preferably 0.2% by mass or higher, more preferably 0.3% by mass or higher, while usually 5% by mass or lower, preferably 3% by mass or lower, more preferably 2% by mass or lower. The thickening agent at a proportion lower than the above range may cause significantly poor easiness of application. The thickening agent at a proportion higher than the above range may cause a low proportion of the active material in the positive electrode active material layer, resulting in a low capacity of the battery and high resistance between the positive electrode active materials.

The conductive material may be any known conductive material. Specific examples thereof include metal materials such as copper and nickel, and carbon materials such as graphite, including natural graphite and artificial graphite, carbon black, including acetylene black, and amorphous carbon, including needle coke. These materials may be used alone or in any combination of two or more at any ratio. The conductive material is used in an amount of usually 0.01% by mass or more, preferably 0.1% by mass or more, more preferably 1% by mass or more, while usually 50% by mass or less, preferably 30% by mass or less, more preferably 15% by mass or less, in the positive electrode active material layer. The conductive material in an amount less than the above range may cause insufficient conductivity. In contrast, the conductive material in an amount more than the above range may cause a low battery capacity.

The solvent for forming slurry may be any solvent that can dissolve or disperse therein the positive electrode active material, the conductive material, and the binder, as well as a thickening agent used as appropriate. The solvent may be either an aqueous solvent or an organic solvent. Examples of the aqueous medium include water and solvent mixtures of an alcohol and water. Examples of the organic medium Include aliphatic hydrocarbons such as hexane; aromatic hydrocarbons such as benzene, toluene, xylene, and methyl naphthalene; heterocyclic compounds such as quinoline and pyridine; ketones such as acetone, methyl ethyl ketone, and cyclohexanone; esters such as methyl acetate and methyl acrylate; amines such as diethylene triamine and N,N-dimethylaminopropyl amine; ethers such as diethyl ether, propylene oxide, and tetrahydrofuran (THF); amides such as N-methylpyrrolidone (NMP), dimethyl formamide, and dimethyl acetamide; and aprotic polar solvents such as hexamethyl phospharamide and dimethyl sulfoxide.

Examples of the material of the current collector for a positive electrode include metal materials such as aluminum, titanium, tantalum, stainless steel, and nickel, and alloys thereof; and carbon materials such as carbon cloth and carbon paper. Preferred is any metal material, especially aluminum or am alloy thereof.

In the case of a metal material, the current collector may be in the form of metal foil, metal cylinder, metal, coil, metal plate, metal film, expanded metal, punched metal, metal, foam, or the like. In the case of a carbon material, it may be in the form of carbon plate, carbon film, carbon cylinder, or the like. Preferred among these is a metal film. The film may be in the form of mesh, as appropriate. The film may have any thickness, and the thickness is usually 1 μm or greater, preferably 3 μm or greater, more preferably 5 μm or greater, while usually 1 mm or smaller, preferably 100 μm or smaller, more preferably 50 μm or smaller. The film having a thickness smaller than the above range may have insufficient strength as a current collector. In contrast, the film having a thickness greater than the above range may have poor handleability.

In order to reduce the electric contact resistance between the current collector and the positive electrode active material layer, the current collector also preferably has a conductive aid applied on the surface thereof. Examples of the conductive aid include carbon and noble metals such as gold, platinum, and silver.

The ratio between the thicknesses of the current collector and the positive electrode active material layer may be any value, and the ratio {(thickness of positive electrode active material layer on one side immediately before injection of electrolyte solution)/(thickness of current collector)} is preferably 20 or lower, more preferably 15 or lower, most preferably 10 or lower. The ratio is also preferably 0.5 or higher, more preferably 0.3 or higher, most preferably 1 or higher. The current collector and the positive electrode active material layer showing a ratio higher than the above range may cause the current collector to generate heat due to Joule heating during high-current-density charge and discharge. The current collector and the positive electrode active material layer showing a ratio lower than the above range may cause an increased ratio by volume of the current collector to the positive electrode active material, reducing the battery capacity.

The positive electrode may be produced by a usual method. An example of the production method is a method in which the positive electrode active material is mixed with the aforementioned binder, thickening agent, conductive material, solvent, and other components to form a slurry-like positive electrode mixture, and then this mixture is applied to a current collector, dried, and pressed so as to be densified.

The densification may be achieved using a manual press or a roll press, for example. The density of the positive electrode active material layer is preferably 1.5 g/cm$^3$ or higher, more preferably 2 g/cm$^3$ or higher, still more preferably 2.2 g/cm$^3$ or higher, while preferably 5 g/cm$^3$ or lower, more preferably 4.5 g/cm³ or lower, still more preferably 4 g/cm³ or lower. The positive electrode active material layer having a density higher than the above range may cause low permeability of the electrolyte solution toward the vicinity of the interface between the current collector and the active material, and poor charge and discharge characteristics particularly at a high current density, failing to provide high output. The positive electrode active material layer having a density lower than the above range may cause poor conductivity between the active materials and increase the battery resistance, failing to provide high output.

In order to improve the stability at high output and high temperature in the case of using the electrolyte solution of the invention, the area of the positive electrode active material layer is preferably large relative to the outer surface area of an external case of the battery. Specifically, the total area of the positive electrode is preferably 15 times or more, more preferably 40 times or more, greater than the surface area of the external case of the secondary battery. For closed, square-shaped cases, the outer surface area of an external case of the battery herein means the total area calculated from the dimensions of length, width, and thickness of the case portion into which a power-generating element is packed except for a protruding portion of a terminal. For closed, cylinder-like cases, the outer surface area of an external case of the battery herein means the geometric surface area of an approximated cylinder of the case portion into which a power-generating element is packed except for a protruding portion of a terminal. The total area of the positive electrode herein means the geometric surface area of the positive electrode mixture layer opposite to a mixture layer including the negative electrode active material. For structures including a current collector foil and positive electrode mixture layers on both sides of the current collector, the total area of the positive electrode is the sum of the areas calculated on the respective sides.

The positive electrode plate may have any thickness. In order to achieve a high capacity and high output, the lower limit of the thickness of the mixture layer on one side of the current collector excluding the thickness of the base metal foil is preferably 10 µm or greater, more preferably 20 µm or greater, while preferably 500 µm or smaller, more preferably 450 µm or smaller.

To a surface of the positive electrode plate may be attached a substance having a composition different from the positive electrode plate. Examples of the substance attached to the surface include oxides such as aluminum oxide, silicon oxide, titanium oxide, zirconium oxide, magnesium oxide, calcium oxide, boron oxide, antimony oxide, and bismuth oxide; sulfates such as lithium sulfate, sodium sulfate, potassium, sulfate, magnesium sulfate, calcium sulfate, and aluminum sulfate; carbonates such as lithium carbonate, calcium carbonate, and magnesium carbonate; and carbon.

<Negative Electrode>

The negative electrode includes a negative electrode active material layer containing a negative electrode active material and a current collector.

Examples of the negative electrode active material include carbonaceous materials that can occlude and release lithium such as pyrolysates of organic matter under various pyrolysis conditions, artificial graphite, and natural graphite; metal oxide materials that can occlude and release lithium such as tin oxide and silicon oxide; lithium metals; various lithium alloys; and lithium-containing metal complex oxide materials. Two or more of these negative electrode active materials may be used in admixture with each other.

The carbonaceous material that can occlude and release lithium is preferably artificial graphite produced by high-temperature treatment of easily graphitizable pitch from various materials, purified natural graphite, or a material obtained by surface treatment on such graphite with pitch or other organic matter and then carbonization of the surface-treated graphite. In order to achieve a good balance between the initial irreversible capacity and the high-current-density charge and discharge characteristics, the carbonaceous material is more preferably selected from carbonaceous materials obtained by heat-treating natural graphite, artificial graphite, artificial carbonaceous substances, or artificial graphite substances at 400° C. to 3200° C. once or more; carbonaceous materials which allow the negative electrode active material layer to include at least two or more carbonaceous matters having different crystallinities and/or have an interface between the carbonaceous matters having the different crystallinities and carbonaceous materials which allow the negative electrode active material layer to have an interface between at least two or more carbonaceous matters having different orientations. These carbonaceous materials may be used alone or in any combination of two or more at any ratio.

Examples of the carbonaceous materials obtained by heat-treating artificial carbonaceous substances or artificial graphite substances at 400° C. to 3200° C. once or more include coal-based coke, petroleum-based coke, coal-based pitch, petroleum-based pitch, and those prepared by oxidizing these pitches; needle coke, pitch coke, and carbon materials prepared by partially graphitizing these cokes; pyrolysates of organic matter such as furnace black, acetylene black, and pitch-based carbon fibers; carbonizable organic matter and carbides thereof; and solutions prepared by dissolving carbonizable organic matter in a low-molecular-weight organic solvent such as benzene, toluene, xylene, quinoline, or n-hexane, and carbides thereof.

The metal material, (excluding lithium-titanium, complex oxides) to be used as the negative electrode active material may be any compound that can occlude and release lithium, and examples thereof include simple lithium, simple metals and alloys that constitute lithium alloys, and oxides, carbides, nitrides, silicides, sulfides, and phosphides thereof. The simple metals and alloys constituting lithium alloys are preferably materials containing any of metal and semi-metal elements in Groups 13 and 14, more preferably simple metal of aluminum, silicon, and tin (hereinafter, referred to as "specific metal elements"), and alloys and compounds containing any of these atoms. These materials may be used alone or in combination of two or more at any ratio.

Examples of the negative electrode active material containing at least one atom selected from the specific metal elements include simple metal of any one specific metal element, alloys of two or more specific metal elements, alloys of one or two or more specific metal elements and one or two or more other metal elements, compounds containing one or two or more specific metal elements, and composite compounds such as oxides, carbides, nitrides, silicides, sulfides, and phosphides of the compounds. Such a simple metal, alloy, or metal compound used as the negative electrode active material can lead to a high-capacity battery.

Examples thereof further include compounds in which any of the above composite compounds are complexly bonded with several elements such as simple metals, alloys, and nonmetal elements. Specifically, in the case of silicon or tin, for example, an alloy of this element and a metal that does not serve as a negative electrode may be used. In the case of tin, for example, a composite compound including a combination of 5 or 6 elements, including tin, a metal (excluding silicon) that serves as a negative electrode, a metal that does not serve as a negative electrode, and a nonmetal element, may be used.

Specific examples thereof include simple Si, $SiB_4$, $SiB_6$, $Mg_2Si$, $Ni_2Si$, $TiSi_2$, $MoSi_2$, $CoSi_2$, $NiSi_2$, $CaSi_2$, $CrSi_2$, $Cu_6Si$, $FeSi_2$, $MnSi_2$, $NbSi_2$, $TaSi_2$, $VSi_2$, $WSi_2$, $ZnSi_2$, SiC, $Si_3N_4$, $Si_2N_2O$, $SiO_v$ ($0<v\leq2$), LiSiO, simple tin, $SnSiO_3$, LiSnO, $Mg_2Sn$, and $SnO_w$ ($0<w\leq2$).

Examples thereof further include composite materials of Si or Sn used as a first constitutional element, and second and third constitutional, elements. The second constitutional element is at least one selected from cobalt, iron, magnesium, titanium, vanadium, chromium, manganese, nickel, copper, zinc, gallium, and zirconium, for example. The third constitutional element is at least one selected from boron, carbon, aluminum, and phosphorus, for example.

In order to achieve a high battery capacity and excellent battery characteristics, the metal material is preferably simple silicon or tin (which may contain trace impurities), $SiO_v$ ($0<v\leq2$), $SnO_w$ ($0\leq w\leq2$), a Si—Co—C composite material, a Si—Ni—C composite material, a Sn—Co—C composite material, or a Sn—Ni—C composite material.

The lithium-containing metal complex oxide material to be used as the negative electrode active material may be any material that can occlude and release lithium. In order to achieve good high-current-density charge and discharge characteristics, materials containing titanium and lithium are preferred, lithium-containing metal complex oxide materials containing titanium are more preferred, and complex oxides of lithium and titanium (hereinafter, abbreviated as "lithium titanium complex oxides") are still more preferred. In other words, use of a spinel-structured lithium titanium complex oxide in the negative electrode active material for an electrolyte battery is particularly preferred because this can markedly reduce the output resistance.

Preferred examples of the lithium titanium complex oxides include compounds represented by the following formula:

$Li_xTi_yM_zO_4$ 

wherein M is at least one element selected from the group consisting of Na, K, Co, Al, Fe, Ti, Mg, Cr, Ga, Cu, Zn, and Nb.

In order to achieve a good balance of the battery performance, particularly preferred among the above compositions are those satisfying any of the following;
(i) $1.2\leq x\leq1.4$, $1.5\leq y\leq1.7$, $z=0$
(ii) $0.9\leq x\leq1.1$, $1.9\leq y\leq2.1$, $z=0$
(iii) $0.7\leq x\leq0.9$, $2.1\leq y\leq2.3$, $z=0$.

Particularly preferred representative composition of the compound is $Li_{4/3}Ti_{5/3}O_4$ corresponding to the composition (i), $Li_1Ti_2O_4$ corresponding to the composition (ii), and $Li_{4/5}Ti_{11/5}O_4$ corresponding to the composition (iii). Preferred examples of the structure satisfying $Z\neq0$ include $Li_{4/3}Ti_{4/3}Al_{1/3}O_4$.

The negative electrode mixture preferably further contains a binder, a thickening agent, and a conductive material. Examples of the binder include the same binders as those mentioned for the positive electrode. The proportion of the binder is preferably 0.1% by mass or more, more preferably 0.5% by mass or more, particularly preferably 0.6% by mass or more, while preferably 20% by mass or less, more preferably 15% by mass or less, still more preferably 10% by mass or less, particularly preferably 8% by mass or less, relative to the negative electrode active material. The binder at a proportion relative to the negative electrode active material higher than the above range may lead to an increased proportion of the binder which fails to contribute to the battery capacity, causing a low battery capacity. The binder at a proportion lower than the above range may cause lowered strength of the negative electrode.

In particular, in the case of using a rubbery polymer typified by SBR as a main component, the proportion of the binder is usually 0.1% fay mass or more, preferably 0.5% by mass or more, more preferably 0.6% by mass or more, while usually 5% by mass or less, preferably 3% by mass or less, more preferably 2% by mass or less, relative to the negative electrode active material. In the case of using a fluoropolymer typified by polyvinylidene fluoride as a main component, the proportion of the binder is usually 1% by mass or more, preferably 2% by mass or more, more preferably 3% by mass or more, while usually 15% by mass or less, preferably 10% by mass or less, more preferably 8% by mass or less, relative to the negative electrode active material.

Examples of the thickening agent include the same thickening agents as those mentioned for the positive electrode. The proportion of the thickening agent is usually 0.1% by mass or higher, preferably 0.5% by mass or higher, still more preferably 0.6% by mass or higher, while usually 5% by mass or lower, preferably 3% by mass or lower, still more preferably 2% by mass or lower, relative to the negative electrode active material. The thickening agent at a proportion relative to the negative electrode active material lower than the above range may cause significantly poor easiness of application. The thickening agent at a proportion higher than the above range may cause a small proportion of the negative electrode active material in the negative electrode active material layer, resulting in a low capacity of the battery and high resistance between the negative electrode active materials.

Examples of the conductive material of the negative electrode include metal materials such as copper and nickel; and carbon materials such as graphite and carbon black.

The solvent for forming slurry may be any solvent that can dissolve or disperse the negative electrode active material and the binder, as well as a thickening agent and a conductive material used as appropriate. The solvent may be either an aqueous solvent or an organic solvent.

Examples of the aqueous solvent include water and alcohols. Examples of the organic solvent include N-methylpyrrolidone (NMP), dimethyl formamide, dimethyl acetamide, methyl ethyl ketone, cyclohexanone, methyl acetate, methyl acrylate, diethyl triamine, N,N-dimethyl aminopropyl amine, tetrahydrofuran (THF), toluene, acetone, diethyl ether, dimethyl acetamide, hexamethyl phospharamide, dimethyl sulfoxide, benzene, xylene, quinoline, pyridine, methyl naphthalene, and hexane.

Examples of the material of the current collector for a negative electrode include copper, nickel, and stainless steel. In order to easily process the material into a film and to minimize the cost, copper is preferred.

The current collector usually has a thickness of 1 μm or greater, preferably 5 μm or greater, while usually 100 μm or smaller, preferably 50 μm or smaller. Too thick a negative electrode current collector may cause an excessive reduction in capacity of the whole battery, while too thin a current collector may be difficult to handle.

The negative electrode may be produced by a usual method. An example of the production method is a method in which the negative electrode material, is mixed with the aforementioned, binder, thickening agent, conductive material, solvent, and other components to form a slurry-like mixture, and then this mixture is applied to a current collector, dried, and pressed so as to be densified. In the case of using an alloyed material, a thin film layer containing the above negative electrode active material (negative electrode active material layer) may be produced by vapor deposition, sputtering, plating, or the like.

The electrode formed from the negative electrode active material may have any structure. The negative electrode active material existing on the current collector preferably has a density of 1 g·cm$^{-3}$ or higher, more preferably 1.2 g·cm$^{-3}$ or higher, particularly preferably 1.3 g·cm$^{-3}$ or higher, while preferably 2.2 g·cm$^{-3}$ or lower, more preferably 2.1 g·cm$^{-3}$ or lower, still more preferably 2.0 g·cm$^{-3}$ or lower, particularly preferably 1.9 g·cm$^{-3}$ or lower. The negative electrode active material existing on the current collector having a density higher than the above range may cause destruction of the negative electrode active material particles, resulting in a high initial irreversible capacity and poor high-current-density charge and discharge characteristics due to reduction in permeability of the electrolyte solution toward the vicinity of the interface between the current collector and the negative electrode active material. The negative electrode active material having a density below the above range may cause poor conductivity between the negative electrode active materials, high battery resistance, and a low capacity per unit volume.

The thickness of the negative electrode plate is a design matter in accordance with the positive electrode plate to be used, and may be any value. The thickness of the mixture layer excluding the thickness of the base metal foil is usually 15 μm or greater, preferably 20 μm or greater, more preferably 30 μm or greater, while usually 300 μm or smaller, preferably 280 μm or smaller, more preferably 250 μm or smaller.

To a surface of the negative electrode plate may be attached a substance having a composition different from the negative electrode plate. Examples of the substance attached to the surface include oxides such as aluminum oxide, silicon oxide, titanium oxide, zirconium oxide, magnesium oxide, calcium oxide, boron oxide, antimony oxide, and bismuth oxide; sulfates such as lithium sulfate, sodium sulfate, potassium sulfate, magnesium sulfate, calcium sulfate, and aluminum sulfate; and carbonates such as lithium carbonate, calcium carbonate, and magnesium carbonate.

<Separator>

The lithium-ion secondary battery preferably further includes a separator.

The separator may be formed from any known material and may have any known shape as long as the resulting separator is stable to the electrolyte solution and is excellent in a liquid-retaining ability. The separator is preferably in the form of a porous sheet or a nonwoven fabric which is formed from a material stable to the electrolyte solution of the invention, such as resin, glass fiber, or inorganic matter, and which has an excellent liquid-retaining ability.

Examples of the material of a resin or glass-fiber separator include polyolefins such as polyethylene and polypropylene, aromatic polyamide, polytetrafluoroethylene, polyether sulfone, and glass filters. These materials may be used alone or in any combination of two or more at any ratio, for example, in the form of a polypropylene/polyethylene bilayer film or a polypropylene/polyethylene/polypropylene trilayer film. In order to achieve good permeability of the electrolyte solution and a good shut-down effect, the separator is preferably a porous sheet or a nonwoven fabric formed from a polyolefin such as polyethylene or polypropylene.

The separator may have any thickness, and the thickness is usually 1 μm or greater, preferably 5 μm or greater, more preferably 8 μm or greater, while usually 50 μm or smaller, preferably 40 μm or smaller, more preferably 30 μm or smaller. The separator thinner than the above range may have poor insulation and mechanical strength. The separator thicker than the above range may cause not only poor battery performance such as poor rate characteristics but also a low energy density of the whole electrolyte battery.

The separator which is a porous one such as a porous sheet or a nonwoven fabric may have any porosity. The porosity is usually 20% or higher, preferably 35% or higher, more preferably 45% or higher, while usually 90% or lower, preferably 85% or lower, more preferably 75% or lower. The separator having a porosity lower than the above range tends to have high film resistance, causing poor rate characteristics. The separator having a porosity higher than the above range tends to have low mechanical strength, causing poor insulation.

The separator may also have any average pore size. The average pore size is usually 0.5 μm or smaller, preferably 0.2 μm or smaller, while usually 0.05 μm or larger. The separator having an average pore size larger than the above range may easily cause short circuits. The separator having an average pore size smaller than the above range may have high film resistance, causing poor rate characteristics.

Examples of the inorganic matter include oxides such as alumina and silicon dioxide, nitrides such as aluminum nitride and silicon nitride, and sulfates such as barium sulfate and calcium sulfate, each in the form of particles or fibers.

The separator is in the form of a thin film such as a nonwoven fabric, a woven fabric, or a microporous film. The thin film favorably has a pore size of 0.01 to 1 μm and a thickness of 5 to 50 μm. Instead of the above separate thin film, the separator may have a structure in which a composite porous layer containing particles of the above inorganic matter is disposed on a surface of one or each of the positive and negative electrodes using a resin binder. For example, alumina particles having a 90% particle size of smaller than 1 μm may be applied to the respective surfaces of the positive electrode with fluororesin used as a binder to form a porous layer.

<Battery Design>

The electrode group may be either a laminate structure including the above positive and negative electrode plates with the above separator in between, or a wound structure including the above positive and negative electrode plates in spiral with the above separator in between. The proportion of the volume of the electrode group in the battery internal volume (hereinafter, referred to as an electrode group proportion) is usually 40% or higher, preferably 50% or higher, while usually 90% or lower, preferably 80% or lower.

The electrode group proportion lower than the above range may cause a low battery capacity. The electrode group proportion higher than the above range may cause small void space in the battery. Thus, if the battery temperature rises to high temperature and thereby the components swell and the liquid fraction of the electrolyte solution exhibits high vapor pressure to raise the internal pressure, the battery characteristics such as charge and discharge repeatability and high-temperature storageability may be impaired and a gas-releasing valve for releasing the internal pressure toward the outside may be actuated.

The current collecting structure may be any structure. In order to more effectively improve the high-current-density charge and discharge performance by the electrolyte solution of the invention, the current collecting structure is preferably a structure which reduces the resistances at wiring portions and jointing portions. Such reduction in internal resistance can particularly favorably lead to the effects achieved with the electrolyte solution of the invention.

In an electrode group having the laminate structure, the metal core portions of the respective electrode layers are preferably bundled and welded to a terminal. If an electrode has a large area, the internal resistance is high. Thus, multiple terminals may preferably be disposed in the electrode so as to reduce the resistance. In an electrode group having the wound structure, multiple lead structures may be disposed on each of the positive electrode and the negative electrode and bundled to a terminal. This can reduce the internal resistance.

The external case may be made of any material that is stable to an electrolyte solution to be used. Specific examples thereof include metals such as nickel-plated steel plates, stainless steel, aluminum and aluminum alloys, and magnesium alloys, and a layered film (laminate film) of resin and aluminum foil. In order to reduce the weight, a metal such as aluminum or an aluminum alloy or a laminate film is favorably used.

An external case made of metal may have a sealed-up structure formed by welding the metal by laser welding, resistance welding, or ultrasonic welding, or a caulking structure using the metal with a resin gasket in between. An external case made of a laminate film may have a sealed-up structure formed by hot-melting resin layers. In order to improve the sealability, a resin which is different from the resin of the laminate film may be disposed between the resin layers. Especially, in the case of forming a sealed-up structure by hot-melting the resin layers with current collecting terminals in between, metal and resin are to be bonded. Thus, the resin to be disposed between the resin layers is favorably a resin having a polar group or a modified resin having a polar group introduced therein.

The lithium-ion secondary battery may have any shape, such as a cylindrical shape, a square shape, a laminate shape, a coin shape, or a large-size shape. The shapes and the structures of the positive electrode, the negative electrode, and the separator may be changed in accordance with the shape of the battery.

A module including the secondary battery is also one aspect of the invention.

In a preferred embodiment, the secondary battery includes a positive electrode, a negative electrode, and the aforementioned electrolyte solution, the positive electrode including a positive electrode current collector and a positive electrode active material layer containing a positive electrode active material, the positive electrode active material containing Mn. The secondary battery including a positive electrode active material layer that contains a positive electrode active material containing Mn can have much better high-temperature storage characteristics.

In order to provide a high-power secondary battery having a high energy density, preferred as the positive electrode active material containing Mn are $LiMn_{1.5}Ni_{0.5}O_4$, $LiNi_{0.5}Co_{0.2}Mn_{0.3}O_2$, and $LiNi_{0.6}Co_{0.2}Mn_{0.2}O_2$.

The amount of the positive electrode active material in the positive electrode active material layer is preferably 80% by mass or more, more preferably 82% by mass or more, particularly preferably 84% by mass or more. The upper limit of the amount thereof is preferably 99% by mass or less, more preferably 98% by mass or less. Too small an amount of the positive electrode active material in the positive electrode active material layer may lead to an insufficient electric capacity. In contrast, too large an amount thereof may lead to insufficient strength of the positive electrode.

The positive electrode active material layer may further contain a conductive material, a thickening agent, and a binder.

The binder may be any material that is safe against a solvent to be used in production of electrodes and the electrolyte solution. Examples thereof include polyvinylidene fluoride, polytetrafluoroethylene, polyethylene, polypropylene, SBR (styrene-butadiene rubber), isoprene rubber, butadiene rubber, ethylene-acrylic acid copolymers, ethylene-methacrylic acid copolymers, polyethylene terephthalate, polymethyl methacrylate, polyimide, aromatic polyamide, cellulose, nitro cellulose, NBR (acrylonitrile-butadiene rubber), fluoroelastomer, ethylene-propylene rubber, styrene-butadiene-styrene block copolymers and hydrogenated products thereof, EPDM (ethylene-propylene-diene terpolymers), styrene-ethylene-butadiene-ethylene copolymers, styrene-isoprene-styrene block copolymers and hydrogenated products thereof, syndiotactic-1,2-polybutadiene, polyvinyl acetate, ethylene-vinyl acetate copolymers, propylene-α-olefin copolymers, fluorinated polyvinylidene fluoride, tetrafluoroethylene-ethylene copolymers, and polymer compositions having ion conductivity of alkali metal ions (especially, lithium ions). These substances may be used alone or in any combination of two or more at any ratio.

The amount of the binder, which is expressed as the proportion of the binder in the positive electrode active material layer, is usually 0.1% by mass or more, preferably 1% by mass or more, more preferably 1.5% by mass or more. The proportion is also usually 80% by mass or less, preferably 60% by mass or less, still more preferably 40% by mass or less, most preferably 10% by mass or less. Too low a proportion of the binder may fail to sufficiently hold the positive electrode active material and cause insufficient mechanical strength of the positive electrode, impairing the battery performance such as cycle characteristics. In contrast, too high a proportion thereof may cause reduction in battery capacity and conductivity.

Examples of the thickening agent include carboxymethyl cellulose, methyl cellulose, hydroxymethyl cellulose, ethyl cellulose, polyvinyl alcohol, oxidized starch, monostarch phosphate, casein, and salts thereof. These agents may be used alone or in any combination of two or more at any ratio.

The proportion of the thickening agent relative to the active material is usually 0.1% by mass or higher, preferably 0.2% by mass or higher, more preferably 0.3% by mass or higher, while usually 5% by mass or lower, preferably 3% by mass or lower, more preferably 2% by mass or lower. The thickening agent at a proportion lower than the above range may cause significantly poor easiness of application. The thickening agent at a proportion higher than the above range may cause a low proportion of the active material in the positive electrode active material layer, resulting in a low capacity of the battery and high resistance between the positive electrode active materials.

The conductive material may be any known conductive material. Specific examples thereof include metal materials such as copper and nickel, and carbon materials such as graphite, including natural graphite and artificial graphite, carbon black, including acetylene black, and amorphous carbon, including needle coke. These materials may be used alone or in any combination of two or more at any ratio. The conductive material is used in an amount of usually 0.01% by mass or more, preferably 0.1% by mass or more, more preferably 1% by mass or more, while usually 50% by mass or less, preferably 30% by mass or less, more preferably 15% by mass or less, in the positive electrode active material layer. The conductive material in an amount less than the above range may cause insufficient conductivity. In contrast, conductive material in an amount more than the above range may cause a low battery capacity.

In order to further improve the high-temperature storage characteristics, the positive electrode current collector is preferably formed from a valve metal or an alloy thereof. Examples of the valve metal include aluminum, titanium, tantalum, and chromium. The positive electrode current collector is more preferably formed from aluminum or an alloy of aluminum.

In order to further improve the high-temperature storage characteristics of the secondary battery, a portion in contact with the electrolyte solution among portions electrically coupled with the positive electrode current collector is also preferably formed from a valve metal or an alloy thereof. In particular, the external case of the battery and a portion that is electrically coupled with the positive electrode current collector and is in contact with the non-aqueous electrolyte solution among components accommodated in the external case of the battery, such as leads and a safety valve, are preferably formed from a valve metal or an alloy thereof. Stainless steel coated with a valve metal or an alloy thereof may also be used.

The positive electrode may be produced by the aforementioned method. An example of the production method is a method in which the positive electrode active material is mixed with the aforementioned binder, thickening agent, conductive material, solvent, and other components to form a slurry-like positive electrode mixture, and then this mixture is applied to a positive electrode current collector, dried, and pressed so as to be densified.

The structure of the negative electrode is as described above.

The electric double-layer capacitor may include a positive electrode, a negative electrode, and the aforementioned electrolyte solution.

At least one selected from the positive electrode and the negative electrode is a polarizable electrode in the electric double-layer capacitor. Examples of the polarizable electrode and a non-polarizable electrode include the following electrodes specifically disclosed in JP H09-7896 A.

The polarizable electrode mainly containing activated carbon to be used in the invention preferably contains inactivated carbon having a large specific surface area and a conductive material, such as carbon black, providing electronic conductivity. The polarizable electrode may be formed by a variety of methods. For example, a polarizable electrode including activated carbon and carbon black can be produced by mixing activated carbon powder, carbon black, and phenolic resin, press-molding the mixture, and then sintering and activating the mixture in an inert gas atmosphere and water vapor atmosphere. Preferably, this polarizable electrode is bonded to a current collector using a conductive adhesive, for example.

Alternatively, a polarizable electrode can also be formed by kneading activated carbon powder, carbon black, and a binder in the presence of an alcohol, forming the mixture into a sheet, and then drying the sheet. The binder to be used may be polytetrafluoroethylene, for example. Alternatively, a polarizable electrode integrated with a current collector can be produced by mixing activated carbon powder, carbon black, a binder, and a solvent to form slurry, applying this slurry to metal foil of a current collector, and then drying the slurry.

The electric double-layer capacitor may have polarizable electrodes mainly containing activated carbon as the respective electrodes. Still, the electric double-layer capacitor may have a structure in which a non-polarizable electrode is used on one side. Examples of such a structure include a structure in which a positive electrode mainly containing an electrode active material such as a metal oxide is combined with a polarizable negative electrode mainly containing activated carbon; and a structure in which a negative electrode mainly containing a carbon material that can reversibly occlude and release lithium ions or a negative electrode of lithium metal or lithium alloy is combined with a polarizable positive electrode mainly containing activated carbon.

In place of or in combination with activated carbon, any carbonaceous material may be used, such as carbon black, graphite, expanded graphite, porous carbon, carbon nanotube, carbon nanohorn, and Ketjenblack.

The non-polarizable electrode is preferably an electrode mainly containing a carbon material that can reversibly occlude and release lithium ions, with this carbon material made to occlude lithium ions in advance. In this case, the electrolyte used is a lithium salt. The s electric double-layer capacitor having such a structure can achieve a much higher withstand voltage exceeding 4 V.

The solvent used in preparation of the slurry in production of electrodes is preferably one that dissolves a binder. In accordance with the type of a binder, the solvent is appropriately selected from N-methylpyrrolidone, dimethyl formamide, toluene, xylene, isophorone, methyl ethyl ketone, ethyl acetate, methyl acetate, dimethyl phthalate, ethanol, methanol, butanol, and water.

Examples of the activated carbon used for the polarizable electrode include phenol resin-type activated carbon, coconut shell-type activated carbon, and petroleum coke-type activated carbon. In order to achieve a large capacity, petroleum coke-type activated carbon or phenol resin-type activated carbon is preferably used. Examples of methods of activating the activated carbon include steam activation and molten KOH activation. In order to achieve a larger capacity, activated carbon prepared fay molten KOH activation is preferably used.

Preferred examples of the conductive agent used for the polarizable electrode include carbon black, Ketjenblack, acetylene black, natural graphite, artificial graphite, metal fiber, conductive titanium oxide, and ruthenium oxide. In order to achieve good conductivity (i.e., low internal resistance), and because too large an amount thereof may lead to a decreased capacity of the product, the amount of the conductive agent such as carbon black used for the polarizable electrode is preferably 1 to 50% by mass in the sum of the amounts of the activated carbon and the conductive agent.

In order to provide an electric double-layer capacitor having a large capacity and low internal resistance, the activated carbon used for the polarizable electrode preferably has an average particle size of 20 μm or smaller and a specific surface area of 1500 to 3000 m$^2$/g. Preferred examples of the carbon material for providing an electrode mainly containing a carbon material that can reversibly occlude and release lithium ions include natural graphite, artificial graphite, graphitized mesocarbon microsphere, graphitized whisker, vapor-grown carbon fiber, sintered furfuryl alcohol resin, and sintered novolak resin.

The current collector may be any chemically and electrochemically corrosion-resistant one. Preferred examples of the current collector used for the polarizable electrode mainly containing activated carbon include stainless steel, aluminum, titanium, and tantalum. Particularly preferred materials in terms of the characteristics and cost of the resulting electric double-layer capacitor are stainless steel and aluminum. Preferred examples of the current collector used for the electrode mainly containing a carbon material that can reversibly occlude and release lithium-ions include stainless steel, copper, and nickel.

Examples of methods of allowing the carbon material that can reversibly occlude and release lithium ions to occlude lithium ions in advance include: (1) a method of mixing powdery lithium to a carbon material that can reversibly occlude and release lithium ions; (2) a method of placing lithium foil on an electrode including a carbon material that can reversibly occlude and release lithium ions and a binder so as to bring the lithium foil to be in electrical contact with the electrode, immersing this electrode in an electrolyte solution containing a lithium salt dissolved therein so as to ionize the lithium, and allowing the carbon material to take in the lithium ions; and (3) a method of placing an electrode including a carbon material that can reversibly occlude and release lithium ions and a binder on the minus side and placing a lithium metal on the plus side, immersing the electrodes in an electrolyte solution containing a lithium salt as an electrolyte, and supplying a current so that the carbon material is allowed to electrochemically take in the ionized lithium.

Examples of known electric double-layer capacitors include wound electric double-layer capacitors, laminated electric double-layer capacitors, and coin-type electric double-layer capacitors. The electric double-layer capacitor may also be any of these types.

For example, a wound electric double-layer capacitor may be assembled as follows. A positive electrode and a negative electrode each of which includes a laminate (electrode) of a current collector and an electrode layer are wound with a separator in between to provide a wound element. This wound element is put into a case made of aluminum, for example. The case is filled, with an electrolyte solution, preferably a non-aqueous electrolyte solution, and then sealed with a rubber sealant.

A separator formed from a conventionally known material and having a conventionally known structure may be used. Examples thereof include polyethylene porous membranes and nonwoven fabric of polypropylene fiber, glass fiber, or cellulose fiber.

In accordance with any known method, the electric double-layer capacitor may be prepared in the form of a laminated electric double-layer capacitor in which sheet-like positive and negative electrodes are stacked with an electrolyte solution and a separator in between or a coin-type electric double-layer capacitor in which positive and negative electrodes are fixed in a coin shape by a gasket with an electrolyte solution and a separator in between.

The electrolyte solution of the invention is useful as an electrolyte solution for large-size lithium-ion secondary batteries for hybrid vehicles or distributed generation, and for electric double-layer capacitors.

EXAMPLES

The invention is described with reference to examples, but the examples are not intended to limit the invention.

The abbreviations in Table 1 and Table 2 represent the following compounds. The blending proportions of the solvents in Table 1 and Table 2 are volume proportions (% by volume) of the components in the solvent, and the blending proportions of the additives are mass proportions (% by mass) of the additives relative to the mass of the solvent in the electrolyte solution.

A: ethylene carbonate
B: ethyl methyl carbonate
C: dimethyl carbonate
D: ethyl propionate
E: fluoroethylene carbonate
F: vinylene carbonate
G: $CH_3OCOOCH_2CF_3$
H: $CHF_2COOCH_3$
I: $CF_3CH_2COOCH_3$
J: tris(trimethylsilyl) phosphite
K: trifluoromethylethylene carbonate
L: 4-(2,2,3,3,3-pentafluoropropyl)1,3-dioxolan-2-one
M: 4-(2,3,3,3-tetrafluoro-2-trifluoromethylpropyl)1,3-dioxolan-2-one Examples and Comparative Examples in Table 1

The components were mixed at proportions shown in Table 1, $LiPF_6$ was added thereto so as to be at a concentration of 1.0 mol/L. Thereby, a non-aqueous electrolyte solution was obtained.

(Production 1 of Positive Electrode)

$LiNi_{1/3}Mn_{1/3}Co_{1/3}O_2$ serving as a positive electrode active material, acetylene black serving as a conductive material, and a dispersion of polyvinylidene fluoride (PVdF) in N-methyl-2-pyrrolidone serving as a binding agent were mixed in a solids content ratio of active material/conductive material/binding agent=92/3/5 (ratio by % by mass). Thereby, positive electrode mixture slurry was prepared. The resulting positive electrode mixture slurry was uniformly applied to a 20-μm-thick aluminum foil current collector and dried. The workpiece was then compression molded, whereby a positive electrode was produced.

(Production of Negative Electrode)

Artificial graphite powder serving as a negative electrode active material, an aqueous dispersion of sodium carboxymethyl cellulose (concentration of sodium carboxymethyl cellulose: 1% by mass) serving as a thickening agent, and an aqueous dispersion of styrene-butadiene rubber (concentration of styrene-butadiene rubber: 50% by mass) serving as a binding agent were mixed in an aqueous solvent in a solids content ratio of active material/thickening agent/binding agent=97.6/1.2/1.2 (ratio by % by mass) to give a mixture in the form of slurry. Thereby, negative electrode mixture slurry was prepared. The negative electrode mixture slurry was uniformly applied to a 20-μm-thick copper foil and dried. The workpiece was then compressed using a press, whereby a negative electrode was produced.

(Production of Lithium Ion Secondary Battery)

The negative electrode and the positive electrode produced as described above and a polyethylene separator were stacked in the order of the negative electrode, the separator, and the positive electrode. Thereby, a battery element was produced.

A bag of a laminate film, which was formed by covering each surface of an aluminum sheet (thickness: 40 μm) with a resin layer, was prepared and the battery element was inserted into the bag with terminals of the positive electrode and the negative electrode protruding therefrom. The bag was charged with an electrolyte solution having the composition shown in Table 1 and sealed in vacuo. Thereby, a sheet-shaped lithium ion secondary battery was produced.
(Measurement of Resistance Increase)

The battery was charged up to a SOC of 50% and discharged at a 5 C rate. The voltage drop (V) during the process was divided by the corresponding current value (A), whereby the IV resistance (Q) was calculated. Then, the battery was charged up to 4.2 V and stored in an open-circuit state at 60° C. for four weeks. The stored battery was adjusted to a SOC of 50% and discharged in the above state at a 5 C rate. The voltage drop (V) during the process was divided by the corresponding current value (A), whereby the IV resistance ($\Omega$) was calculated. In each example, the ratio of the values before storage and after storage was calculated. The value in Example 4 was taken as 100, and was compared with the values of the respective examples.

The term SOC means the state of charge, and a SOC of 100% means the capacity of the battery charged up to 4.2 V. For example, a SOC of 50% means half the capacity of a SOC of 100%.

Table 1 shows the results.

to a 20-μm-thick aluminum foil current collector and dried. The workpiece was then compression molded, whereby a positive electrode was produced.
(Production of Negative Electrode)

Artificial graphite powder serving as a negative electrode active material, an aqueous dispersion of sodium carboxymethyl cellulose (concentration of sodium carboxymethyl cellulose: 1% by mass) serving as a thickening agent, and an aqueous dispersion of styrene-butadiene rubber (concentration of styrene-butadiene rubber: 50% by mass) serving as a binding agent, were mixed in an aqueous solvent in a solids content ratio of active material/thickening agent/binding agent=97.6/1.2/1.2 (ratio by % by mass) to give a mixture in the form of slurry. Thereby, negative electrode mixture slurry was prepared. The negative electrode mixture slurry was uniformly applied to a 20-μm-thick copper foil and dried. The workpiece was then compressed using a press, whereby a negative electrode was produced.
(Production of Lithium Ion Secondary Battery)

The negative electrode and the positive electrode produced as described above and a polyethylene separator were

TABLE 1

| | Solvent | | | | Additive | | | | | |
| --- | --- | --- | --- | --- | --- | --- | --- | --- | --- | --- |
| | Type | Blending proportion (vol %) | Type | Blending proportion (vol %) | Type | Blending proportion (mass %) | Type | Blending proportion (mass %) | Type | Blending proportion (mass %) | Resistance Increase |
| Example 1 | A | 30 | B | 70 | J | 0.001 | L | 0.5 | — | 0 | 106 |
| Example 2 | A | 30 | B | 70 | J | 0.01 | L | 0.5 | — | 0 | 104 |
| Example 3 | A | 30 | B | 70 | J | 0.1 | L | 0.5 | — | 0 | 103 |
| Example 4 | A | 30 | B | 70 | J | 0.5 | L | 0.5 | — | 0 | 100 |
| Example 5 | A | 30 | B | 70 | J | 1 | L | 0.5 | — | 0 | 108 |
| Example 6 | A | 30 | B | 70 | J | 10 | L | 0.5 | — | 0 | 107 |
| Example 7 | A | 30 | B | 70 | J | 0.5 | L | 0.001 | — | 0 | 105 |
| Example 8 | A | 30 | B | 70 | J | 0.5 | L | 0.01 | — | 0 | 104 |
| Example 9 | A | 30 | B | 70 | J | 0.5 | L | 0.1 | — | 0 | 103 |
| Example 10 | A | 30 | B | 70 | J | 0.5 | L | 1 | — | 0 | 102 |
| Example 11 | A | 30 | B | 70 | J | 0.5 | L | 10 | — | 0 | 105 |
| Example 12 | A | 30 | B | 70 | J | 0.5 | L | 0.5 | F | 0.001 | 92 |
| Example 13 | A | 30 | B | 70 | J | 0.5 | L | 0.5 | F | 0.01 | 91 |
| Example 14 | A | 30 | B | 70 | J | 0.5 | L | 0.5 | F | 0.1 | 90 |
| Example 15 | A | 30 | B | 70 | J | 0.5 | L | 0.5 | F | 0.5 | 89 |
| Example 16 | A | 30 | B | 70 | J | 0.5 | L | 0.5 | F | 1 | 90 |
| Example 17 | A | 30 | B | 70 | J | 0.5 | L | 0.5 | F | 10 | 93 |
| Example 18 | A | 30 | B | 70 | J | 0.5 | M | 0.5 | — | 0 | 101 |
| Example 19 | A | 30 | B | 70 | J | 0.5 | M | 0.5 | F | 0.5 | 90 |
| Example 20 | A | 30 | C | 70 | J | 0.5 | L | 0.5 | — | 0 | 102 |
| Example 21 | A | 30 | C | 70 | J | 0.5 | L | 0.5 | F | 0.5 | 91 |
| Example 22 | A | 30 | D | 70 | J | 0.5 | L | 0.5 | — | 0 | 103 |
| Example 23 | A | 30 | D | 70 | J | 0.5 | L | 0.5 | F | 0.5 | 92 |
| Comparative Example 1 | A | 30 | B | 70 | J | 0.5 | — | 0 | — | 0 | 124 |
| Comparative Example 2 | A | 30 | B | 70 | J | 0.5 | — | 0 | F | 0.5 | 119 |
| Comparative Example 3 | A | 30 | B | 70 | — | 0 | L | 0.5 | — | 0 | 125 |
| Comparative Example 4 | A | 30 | B | 70 | — | 0 | L | 0.5 | F | 0.5 | 120 |

Examples and Comparative Examples in Table 2

The components were mixed at proportions shown in Table 2, LiPF$_6$ was added thereto so as to be at a concentration of 1.0 mol/L. Thereby, a non-aqueous electrolyte solution was obtained.
(Production 2 of Positive Electrode)

LiNi$_{0.5}$Mn$_{1.5}$O$_4$ serving as a positive electrode active material, acetylene black serving as a conductive material, and a dispersion of polyvinylidene fluoride (PVdF) in methyl-2-pyrrolidone serving as a binding agent were mixed in a solids content ratio of active material/conductive material/binding agent=92/3/5 (ratio by % by mass). Thereby, positive electrode mixture slurry was prepared. The resulting positive electrode mixture slurry was uniformly applied stacked in the order of the negative electrode, the separator, and the positive electrode. Thereby, a battery element was produced.

A bag of a laminate film, which was formed by covering each surface of an aluminum sheet (thickness: 40 μm) with a resin layer, was prepared and the battery element was inserted into the bag with terminals of the positive electrode and the negative electrode protruding therefrom. The bag was charged with an electrolyte solution having the composition shown in Table 2 and sealed in vacuo. Thereby, a sheet-shaped lithium ion secondary battery was produced.
(Measurement of Resistance Increase)

The battery was adjusted up to a SOC of 50% and discharged at a 5 C rate. The voltage drop (V) during the process was divided by the corresponding current value (A), whereby the IV resistance (Q) was calculated. Then, the battery was charged up to 4.9 V and stored in an open-circuit state at 60° C. for four weeks. The stored battery was adjusted to a SOC of 50% and discharged in the above state at a 5 C rate. The voltage drop (V) during the process was divided by the corresponding current value (A), whereby the IV resistance (Q) was calculated. In each example, the ratio of the values before storage and after storage was calculated. The value in Example 27 was taken as 100, and was compared with the values of the respective examples.

The term SOC means the state of charge, and a SOC of 100% means the capacity of the battery charged up to 4.9 V. For example, a SOC of 50% means half the capacity of a SOC of 100%.

Table 2 shows the results.

the compound (1-b) being represented by the following formula:

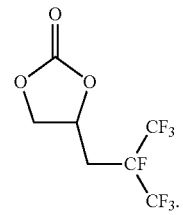

TABLE 2

|  | Solvent | | | | Additive | | | | | |
| --- | --- | --- | --- | --- | --- | --- | --- | --- | --- | --- |
|  | Type | Blending proportion (vol %) | Type | Blending proportion (vol %) | Type | Blending proportion (mass %) | Type | Blending proportion (mass %) | Type | Blending proportion (mass %) | Resistance Increase |
| Example 24 | E | 30 | G | 70 | J | 0.001 | L | 0.5 | — | 0 | 105 |
| Example 25 | E | 30 | G | 70 | J | 0.01 | L | 0.5 | — | 0 | 103 |
| Example 26 | E | 30 | G | 70 | J | 0.1 | L | 0.5 | — | 0 | 101 |
| Example 27 | E | 30 | G | 70 | J | 0.5 | L | 0.5 | — | 0 | 100 |
| Example 28 | E | 30 | G | 70 | J | 1 | L | 0.5 | — | 0 | 101 |
| Example 29 | E | 30 | G | 70 | J | 10 | L | 0.5 | — | 0 | 106 |
| Example 30 | E | 30 | G | 70 | J | 0.5 | L | 0.001 | — | 0 | 106 |
| Example 31 | E | 30 | G | 70 | J | 0.5 | L | 0.01 | — | 0 | 105 |
| Example 32 | E | 30 | G | 70 | J | 0.5 | L | 0.1 | — | 0 | 102 |
| Example 33 | E | 30 | G | 70 | J | 0.5 | L | 1 | — | 0 | 102 |
| Example 34 | E | 30 | G | 70 | J | 0.5 | L | 10 | — | 0 | 106 |
| Example 35 | E | 30 | G | 70 | J | 0.5 | L | 0.5 | F | 0.001 | 86 |
| Example 36 | E | 30 | G | 70 | J | 0.5 | L | 0.5 | F | 0.01 | 87 |
| Example 37 | E | 30 | G | 70 | J | 0.5 | L | 0.5 | F | 0.1 | 86 |
| Example 38 | E | 30 | G | 70 | J | 0.5 | L | 0.5 | F | 0.5 | 85 |
| Example 39 | E | 30 | G | 70 | J | 0.5 | L | 0.5 | F | 1 | 86 |
| Example 40 | E | 30 | G | 70 | J | 0.5 | L | 0.5 | F | 10 | 89 |
| Example 41 | E | 30 | G | 70 | J | 0.5 | M | 0.5 | — | 0 | 101 |
| Example 42 | E | 30 | G | 70 | J | 0.5 | M | 0.5 | F | 0.5 | 87 |
| Example 43 | K | 30 | G | 70 | J | 0.5 | L | 0.5 | — | 0 | 101 |
| Example 44 | K | 30 | G | 70 | J | 0.5 | L | 0.5 | F | 0.5 | 87 |
| Example 45 | E | 30 | H | 70 | J | 0.5 | L | 0.5 | — | 0 | 102 |
| Example 46 | E | 30 | H | 70 | J | 0.5 | L | 0.5 | F | 0.5 | 88 |
| Example 47 | E | 30 | I | 70 | J | 0.5 | L | 0.5 | — | 0 | 102 |
| Example 48 | E | 30 | I | 70 | J | 0.5 | L | 0.5 | F | 0.5 | 89 |
| Example 49 | K | 30 | H | 70 | J | 0.5 | L | 0.5 | — | 0 | 103 |
| Example 50 | K | 30 | H | 70 | J | 0.5 | L | 0.5 | F | 0.5 | 90 |
| Comparative Example 5 | E | 30 | G | 70 | J | 0.5 | — | 0 | — | 0 | 136 |
| Comparative Example 6 | E | 30 | G | 70 | J | 0.5 | — | 0 | F | 0.5 | 134 |
| Comparative Example 7 | E | 30 | G | 70 | — | 0 | L | 0.5 | — | 0 | 138 |
| Comparative Example 8 | E | 30 | G | 70 | — | 0 | L | 0.5 | F | 0.5 | 136 |

The invention claimed is:

1. An electrolyte solution comprising a solvent and additives comprising tris(trimethylsilyl) phosphite in an amount of 0.001-10% by mass relative to the solvent and at least one fluorinated saturated cyclic carbonate (1) in an amount of 0.001-10% by mass relative to the solvent selected from the group consisting of a compound (1-a) and a compound (1-b), the compound (1-a) being represented by the following formula:

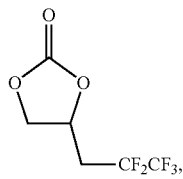

2. The electrolyte solution according to claim 1, wherein the solvent contains at least one selected from the group consisting of a non-fluorinated saturated cyclic carbonate, a fluorinated saturated cyclic carbonate other than the fluorinated saturated cyclic carbonate (1), a non-fluorinated acyclic carbonate, a fluorinated acyclic carbonate, a non-fluorinated acyclic ester, and a fluorinated acyclic ester.

3. The electrolyte solution according to claim 1, further comprising vinylene carbonate in an amount of 0.001-10% by mass relative to the solvent.

4. The electrolyte solution according to claim 1, further comprising an electrolyte salt.

5. An electrochemical device comprising the electrolyte solution according to claim 1.

6. A module comprising the electrochemical device according to claim 5.

7. A secondary battery comprising the electrolyte solution according to claim 1.

8. A module comprising the secondary battery according to claim 7.

* * * * *